(12) United States Patent
Turcott

(10) Patent No.: US 7,194,306 B1
(45) Date of Patent: Mar. 20, 2007

(54) CARDIAC OPTIMIZATION THROUGH LOW-FREQUENCY ANALYSIS OF HEMODYNAMIC VARIABLES

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 455 days.

(21) Appl. No.: 10/656,603

(22) Filed: Sep. 5, 2003

(51) Int. Cl.
*A61N 1/365* (2006.01)

(52) U.S. Cl. .............................. 607/17; 607/18; 607/9

(58) Field of Classification Search .................. None
See application file for complete search history.

(56) References Cited

U.S. PATENT DOCUMENTS

| | | | |
|---|---|---|---|
| 5,044,366 A * | 9/1991 | Alt | 607/18 |
| 5,466,245 A * | 11/1995 | Spinelli et al. | 607/17 |
| 5,487,752 A | 1/1996 | Salo et al. | 607/17 |
| 6,096,061 A * | 8/2000 | Alt et al. | 607/4 |
| 6,409,675 B1 | 6/2002 | Turcott | 600/508 |
| 6,477,406 B1 | 11/2002 | Turcott | 600/518 |
| 6,491,639 B1 | 12/2002 | Turcott | 600/508 |
| 6,522,923 B1 | 2/2003 | Turcott | 607/27 |
| 6,527,729 B1 | 3/2003 | Turcott | 600/528 |
| 6,567,700 B1 | 5/2003 | Turcott et al. | 507/9 |
| 6,575,912 B1 | 6/2003 | Turcott | 600/485 |
| 2003/0105499 A1 * | 6/2003 | Hartley et al. | 607/17 |

OTHER PUBLICATIONS

Mestan, et al., "A New Method of Estimation of the Optimal AV Delay by Using Pulse Oximetry in DDD Paced Patients", Acta Medica (Hradec Karlove) 41:135-139 (1998).
Fargell, et al., "Non-Invasive Beat-to-Beat Analysis of Stroke Volume and Digital Pulse Volume in Patients with Complete Heart Block and Artificial Pacing," Acta Medica (Scand) 205:185-190 (1979).
Eliakim, et al., "Assessment of the Atrial Contribution to Cardiac Performance by a Noninvasive Photoplethysmographic Technique," Cardiology 58:7-13 (1973).

* cited by examiner

*Primary Examiner*—Carl Layno
(74) *Attorney, Agent, or Firm*—Steven M. Mitchell

(57) ABSTRACT

A parameter in an implantable cardiac therapy device (ICTD) is optimized based on analysis of a hemodynamic signal. The method includes receiving a hemodynamic signal; filtering the hemodynamic signal data to isolate low frequency data present therein; and sampling the low frequency data according to a sampling algorithm. The parameter is optimized in the ICTD based on an analysis of the sampled low frequency data.

33 Claims, 16 Drawing Sheets

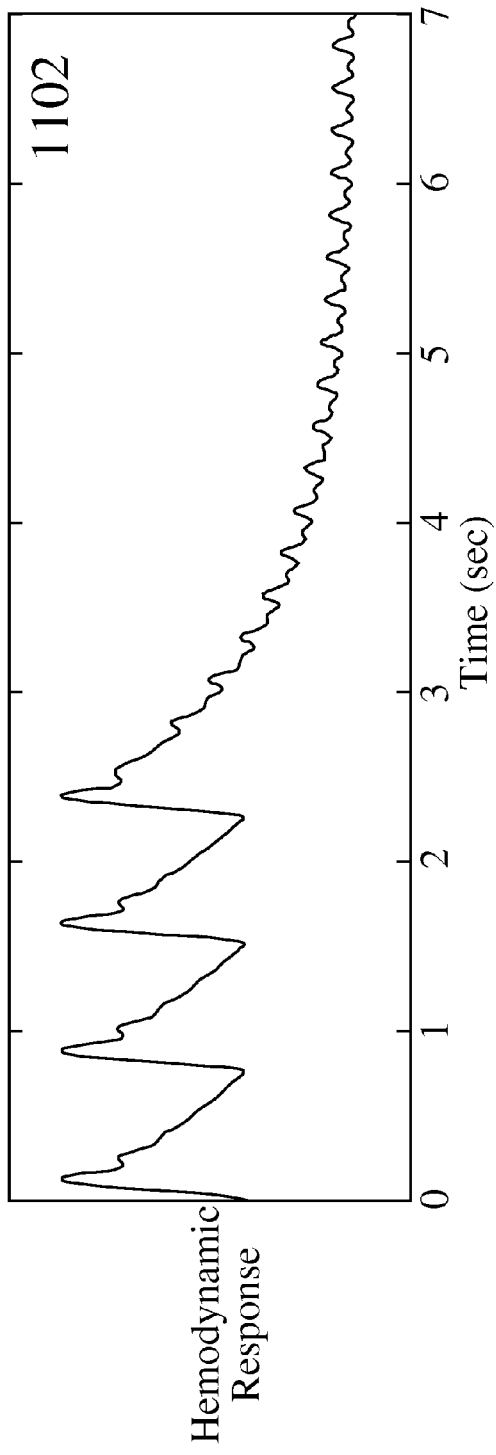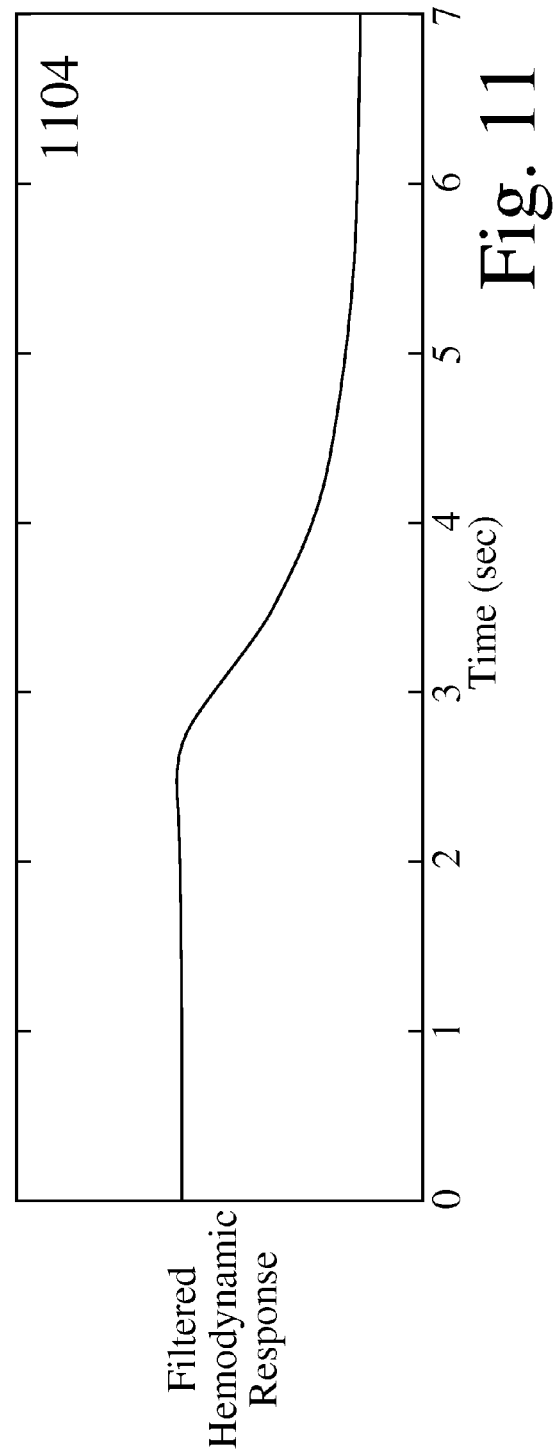
Fig. 11

CARDIAC OPTIMIZATION THROUGH LOW-FREQUENCY ANALYSIS OF HEMODYNAMIC VARIABLES

BACKGROUND OF THE INVENTION

1. Field of the Invention

The present invention relates to methods and devices for optimizing hemodynamic variables in implantable cardiac therapy devices (ICTDs). More particularly, the present invention uses a low frequency analysis of various hemodynamic variables to optimize ICTD performance.

2. Background Art

An implantable cardiac therapy device (ICTD) is a medical device that is implanted in a patient to monitor electrical activity of the heart and to deliver appropriate electrical and/or drug therapy, as required. ICTDs include, for example, pacemakers and cardioverter defibrillators.

ICTDs are in electrical communication with the heart. To deliver effective therapy, ICTDs use various forms of physiological information and feedback. Volumetric changes in blood flow and changes in blood pressure, which are closely related, are sources of physiological information that can be used to optimize ICTD performance. Plethysmography is one technique that provides information on volumetric changes in blood flow and changes in blood pressure.

Plethysmography is a generic term referring to a variety of techniques for monitoring volume changes. For example, plethysmography has been used to measure volume changes of the lungs due to respiration, or volume changes in blood in vessels of a limb or tissue segment. When applied to measurements of blood volume in living animals, changes occur in a pulsatile manner with each beat of the heart as blood flows in and out of a portion of the body. The study of vascular activity by fluid displacement methods dates back to at least 1890. Some contemporary techniques include strain gauge, pneumatic, impedance, Doppler, and photoelectric plethysmography. When applied to a body, a plethysmography device produces a waveform that is similar to an arterial pressure waveform as volume changes and pressure changes in fluid are closely related. This waveform is useful in measuring pulse velocity and indicating arterial obstructions.

Plethysmography is a convenient source of information because it can be non-invasive. Furthermore, even when a particular plethysmography technique is invasive, it remains extra-vascular, and thus eliminates various risks associated with intra-vascular measurements such as thrombus, embolus, infections and internal bleeding.

Conventional attempts to use plethysmography to optimize ICTD performance have focused on pulse amplitude. The pulse signal occupies the frequency band of approximately one to ten Hertz (Hz) in the plethysmography signal spectrum. Pulse amplitude is an appealing measure because it directly reflects the contractility and mechanical efficiency of the heart. However, it is sensitive to numerous sources of variability, such as respiration and intrinsic fluctuations in sympathetic outflow (Meyer waves). More importantly, the pulse amplitude can increase even as the mean arterial pressure falls, so that decreases in hemodynamic function can be misinterpreted. It would be beneficial to obtain plethysmographic data that is insensitive to the above sources of variability.

BRIEF SUMMARY OF THE INVENTION

The invention uses plethysmography, blood pressure, or other hemodynamic signals to optimize performance of implantable cardiac tharapy devices (ICTDs). In a preferred embodiment, the invention uses an unconventional, low frequency portion of the hemodynamic signal to optimize ICTD performance. Preferably, the invention uses the portion of the hemodynamic signal in the range of about 0.03 Hz to about 1.0 Hz and, more preferably, in the range of about 0.1 Hz to about 1.0 Hz. From the low frequency data, ICTD parameters such as atrio-ventricular and inter-ventricular delays, arrhythmia therapy voltage levels, ICTD lead placement, and pacing rate cutoff may be optimized.

A method is disclosed for optimizing a parameter in an implantable cardiac therapy device. The method comprises receiving a hemodynamic signal; filtering the hemodynamic signal to isolate low frequency data present in the frequency spectrum; and sampling the low frequency data according to a sampling algorithm. The parameter is optimized in the ICTD based on an analysis of the sampled low frequency data. The sampling algorithm depends on which parameter is to be optimized.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements.

FIG. 1A demonstrates the environment in which the present invention may be used.

FIG. 11 illustrates the onset of a hemodynamically unstable arrhythmia.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein. Before describing the invention in detail, it is helpful to describe an example environment in which the invention may be implemented.

A. Implantable Cardiac Therapy Devices

The present invention is particularly useful in the environment of an implantable cardiac therapy device. Implantable cardiac therapy devices include, for example, pacemakers and cardioverter defibrillators. The term "implantable cardiac therapy device" or simply "ICTD" is used herein to refer to any pacemaker or implantable cardioverter defibrillator (ICD). FIGS. 1A and 1B, and FIGS. 2A and 2B illustrate such an environment.

Figure 1A:
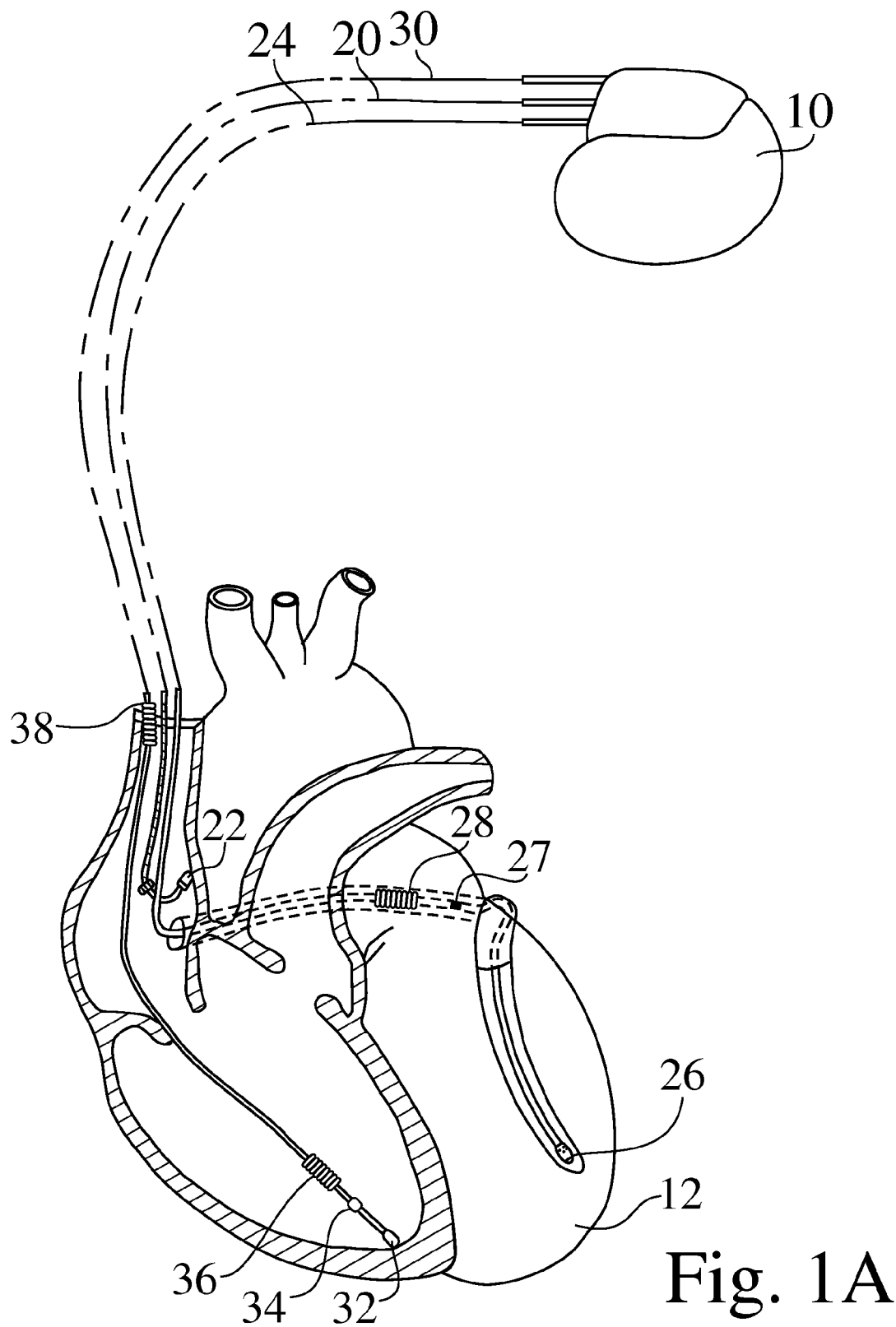
FIG. 1B is a simplified block diagram of an implantable cardiac therapy device.

As shown in FIG. 1A, there is an exemplary ICTD 10 in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICTD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICTD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICTD 10 is also shown in electrical communication with the patient's heart 12 by way of an implantable right ventricular lead 30 having a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the superior vena cava. Accordingly, right ventricular lead 30 is capable of receiving cardiac signals and delivering stimulation in the form of pacing and shock therapy to the right ventricle.

Figure 1B:
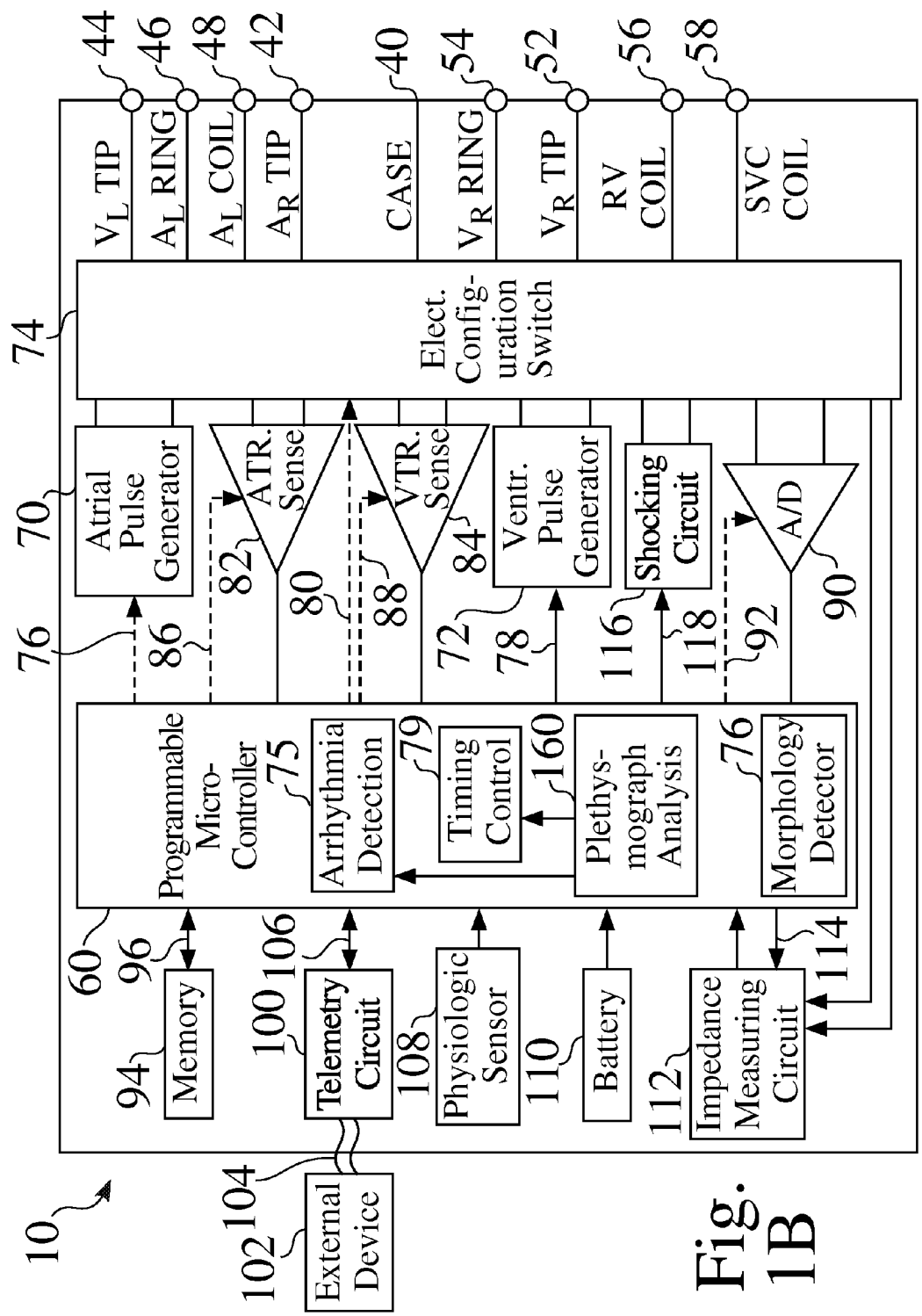

FIG. 1B shows a simplified block diagram of ICTD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICTD 10, shown schematically in FIG. 1B, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICTD 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art. In a specific embodiment of the present invention, the micro processor has a functional block for analyzing plethysmography data 160.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the ICTD's and their inter-relationship, see U.S. Pat. No. 4,788,980 (Mann et al. et al.). The '052, '555, '298 and '980 patents are incorporated herein by reference.

As shown in FIG. 1B, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 76 and 78, respectively, to trigger or inhibit the stimulation pulses. Power for the microcontroller 60, as well as for the various pulse generators supplied by a battery 110.

Microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) interval, interatrial (RA-LA) interval, and pacing rate. According to the present invention, optimization of these parameters may be achieved by plethysmograph analysis as described further detail below.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICTD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICTD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, morphology, etc.) in order to determine the type of remedial therapy that is needed (e.g., bradycardia pacing, anti-tachycardia pacing, cardioversion shocks or defibrillation shocks, collectively referred to as "tiered therapy"). According to the present invention, photo-plethysmography provides an additional source of information for optimization of ICTD performance for arrhythmia therapy.

Microcontroller 60 utilizes arrhythmia detection circuitry 75 and morphology detection circuitry 76, as well as plethysmography analysis circuitry 160, to recognize and classify arrhythmia so that appropriate therapy can be delivered.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Advantageously, data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969, 467 (Callaghan et al. et al.); and U.S. Pat. No. 5,350,410

(Kleks et al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICTD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of ICTD 10 may be non-invasively programmed into memory 94 through a telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICTD 10 (as contained in microcontroller 60 or memory 94) to be sent to external device 102 through an established communication link 104.

For examples of such devices, see U.S. Pat. No. 4,809, 697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

Telemetry circuit 100 also allows optimization parameters obtained externally to be sent into micro-controller 60. For example, plethysmography data obtained by an external plethysmography device could be passed to micro-controller 60 for analysis and optimization of a number of parameters, as discussed below.

In the preferred embodiment, ICTD 10 further includes a physiologic sensor 108, that can be used to detect changes in cardiac performance or changes in the physiological condition of the heart. Accordingly, microcontroller 60 can respond by adjusting the various pacing parameters (such as rate, AV Delay, RV-LV interval, etc.) in accordance with the embodiments of the present invention. Microcontroller 60 controls adjustments of pacing parameters by, for example, controlling the stimulation pulses generated by the atrial and ventricular pulse generators 70 and 72. While shown as being included within ICTD 10, it is to be understood that physiologic sensor 108 may also be external to ICTD 10, yet still be implanted within or carried by the patient. More specifically, sensor 108 can be located inside ICTD 10, on the surface of ICTD 10, in a header of ICTD 10, or on a lead (which can be placed inside or outside the bloodstream). In one embodiment of the present invention, physiologic sensor 108 is an implantable extra-vascular photoplethysmography device.

ICTD 10 further includes a magnet detection circuitry (not shown), coupled to microcontroller 60. It is the purpose of the magnet detection circuitry to detect when a magnet is placed over ICTD 10, which magnet may be used by a clinician to perform various test functions of ICTD 10 and/or to signal microcontroller 60 that the external programmer 102 is in place to receive or transmit data to microcontroller 60 through telemetry circuit 100.

As further shown in FIG. 1B, ICTD 10 is shown as having an impedance measuring circuit 112 which is enabled by microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to switch 74 so that any desired electrode may be used. The impedance measuring circuit 112 is not critical to the present invention and is shown only for completeness.

In the case where ICTD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

B. Photoplethysmography

Figure 2:
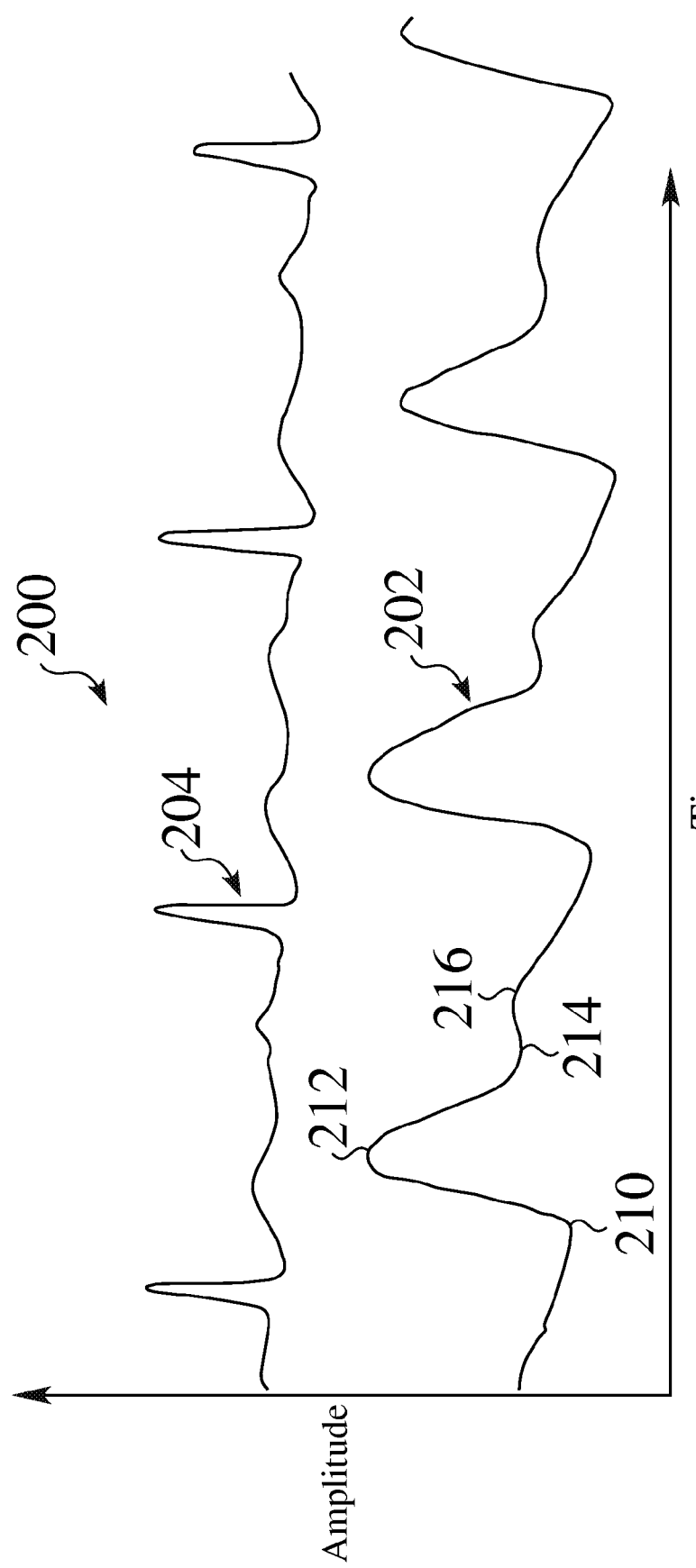
FIG. 2 illustrates an exemplary plethysmograph.

FIG. 2 illustrates an exemplary plethysmograph 200, which includes a hemodynamic waveform 202 produced by a plethysmography device. For timing reference, an electrocardiogram (ECG) signal 204 is illustrated. Hemodynamic waveform 202 provides a measure of the volume of the arterial vasculature. A measure of arterial pulse amplitude is derived from it. A few tens to a few hundreds of milliseconds after the QRS complex, the plethysmography voltage reaches a minimum 210 and starts to increase. This is due to the increasing blood volume in the arterioles as the systolic pulse reaches the periphery. The delay is influenced by the distance that the sensor is placed from the heart. It requires approximately 100 msec for the waveform to reach its maximum 212. The excursion from minimum 210 to maximum 212 represents the arterial pulse amplitude. During diastole, the recoil of the elastic arterial vessels continues to force blood through the capillaries, so that blood flows through the capillary bed throughout the entire cardiac cycle.

A photoplethysmography device (PPG) (also called a pseudoplethysmography or photoelectric plethysmography device) includes a light detector and a light source. The PPG utilizes the transmission or reflection of light to demonstrate the hemodynamic changes in blood perfusion. Such devices might be used in the cardiology department or intensive care department of a hospital or in a clinic for diagnostic purposes related to vascular surgery. According to the present invention, low frequency analysis of this hemodynamic signal, on the order of about 0.03 Hz to about 1.0 Hz and, more preferably, about 0.1 Hz to about 1.0 Hz, may also be used to provide optimization feedback directly to an ICTD 10. A photoplethysmography device is also referred to, herein, simply as a plethysmography device.

Figure 3A:
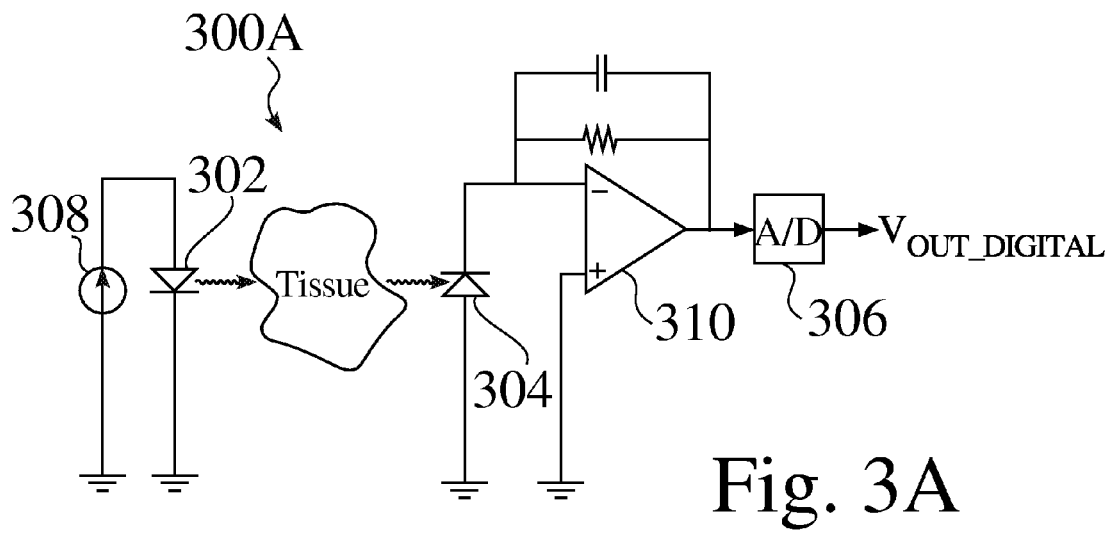
FIG. 3A is a simplified block diagram of a conventional photoplethysmography device.
Figure 3B:
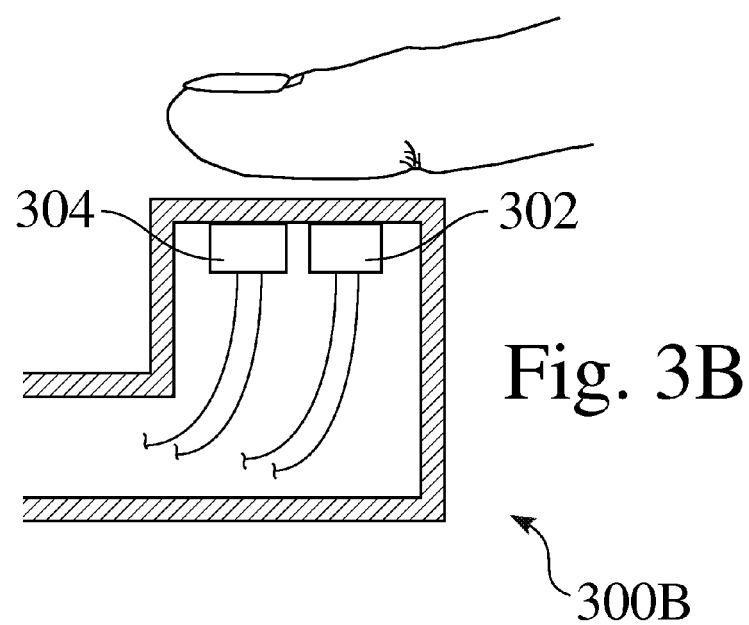
FIG. 3B is an exemplary mechanical arrangement for a conventional photoplethysmography device.

An exemplary circuit 300A for a conventional photoplethysmography device is shown in FIG. 3A. An exemplary mechanical arrangement 300B for a conventional external photoplethysmography device is shown in FIG. 3B. In these examples, the light source is a light-emitting diode (LED) 302 excited by a constant current source 308, although in alternative models an incandescent lamp, laser, or laser diode can be used as the light source. The light detector in this example is a photodiode 304. Changes in the received light intensity cause proportional changes in the current through the photodiode 304. An operational amplifier 310, configured as a transimpedance amplifier, filters the LED current and converts it to an analog voltage. This varying analog voltage is typically converted to a digital signal ($V_{out\_digital}$) using an analog to digital converter (A/D) 306. Other known light detectors include photo resistors, photo transistors, photo Darlingtons and avalanche photodiodes. Light detectors are often also referred to as photo detectors or photo cells.

Light may be transmitted through a capillary bed such as in an ear lobe or finger tip. Additionally, a PPG may be implanted. An implanted PPG confers various benefits. Because an implanted PPG remains extra-vascular (outside the blood stream), it reduces the risks associated with intra-vascular (inside the blood stream) measurements. Risks of intra-vascular measurement include thrombus (clotted artery), embolus (clot breaks free and floats down artery), infection and internal bleeding.

In both external and implantable devices, as arterial pulsations cause expansion and contraction of the arterioles and other blood vessels, changes in volume of the blood vessels modify the absorption, reflection and scattering of the light. Stated another way, an arterial pulse in, for example, a finger tip, or ear lobe, causes blood volume to change, thereby changing the optical density of the tissue. Therefore, the arterial pulse modulates the intensity of the light passing through the tissue. In the reflectance-mode configuration illustrated in FIG. 3B, light from LED 302 is reflected into photoresistor 304 by scattering and/or by direct reflection from underlying tissue.

It is noted that photoplethysmography devices may operate in either a transmission configuration or a reflection configuration. In the transmission configuration, the light source (e.g., LED 302) and the photodetector (e.g., 304) face one another and a segment of the body (e.g., a finger or earlobe) is interposed between the source and detector. In the reflection configuration, the light source (e.g., LED 302) and photodetector (e.g., 304) are mounted adjacent to one another, e.g., on the surface of the body, as shown in FIG. 3B. If the photoplethysmography device is incorporated into an implantable cardiac therapy device or monitor, and thus implanted, then the light source (e.g., LED 302) and light detector (e.g., 304) can be mounted adjacent to one another on the housing (e.g., can) or header of the ICTD, as disclosed in U.S. Pat. No. 6,491,639, entitled "Extravascular Hemodynamic Sensor", filed Apr. 5, 2000, which is incorporated herein by reference in its entirety.

Conventionally, PPGs do not provide "calibratable" value changes. Thus, their usefulness is generally limited to pulse-velocity measurements, determination of heart rate, and an indication of the existence of a pulse (e.g., in a finger). Additionally, a conventional PPG provides a poor measure of changes in volume and is very sensitive to motion artifacts, respiration, and intrinsic fluctuations in sympathetic outflow (Meyer waves). In fact, the pulse amplitude can increase even as the mean arterial pressure falls, so that decreases in hemodynamic function can be misinterpreted. However, according to the present invention, low frequency analysis of a conventionally produced plethysmogram solves many of the problems encountered in conventional plethysmogram analysis. This is further described below.

C. Low Frequency Analysis of Hemodynamic Signals Generally

Hemodynamic signals are signals related to blood flow that vary as the heart beats. Generally hemodynamic signals come from measuring parameters such as blood pressure or volume changes, or from noise and flow measurements such as an echocardiogram. Thus, traditional analysis of these signals has focused on the frequency range that represents a beating heart, e.g., one to ten Hertz, or represent average or dc values, which correspond to zero Hertz. The present invention recognizes that valuable information also resides in a low frequency portion of the hemodynamic frequency spectrum, e.g., below about one Hertz, but above dc. This low frequency information can be used, for example, as feedback to an implantable cardiac therapy device (ICTD) 10.

Figure 4:
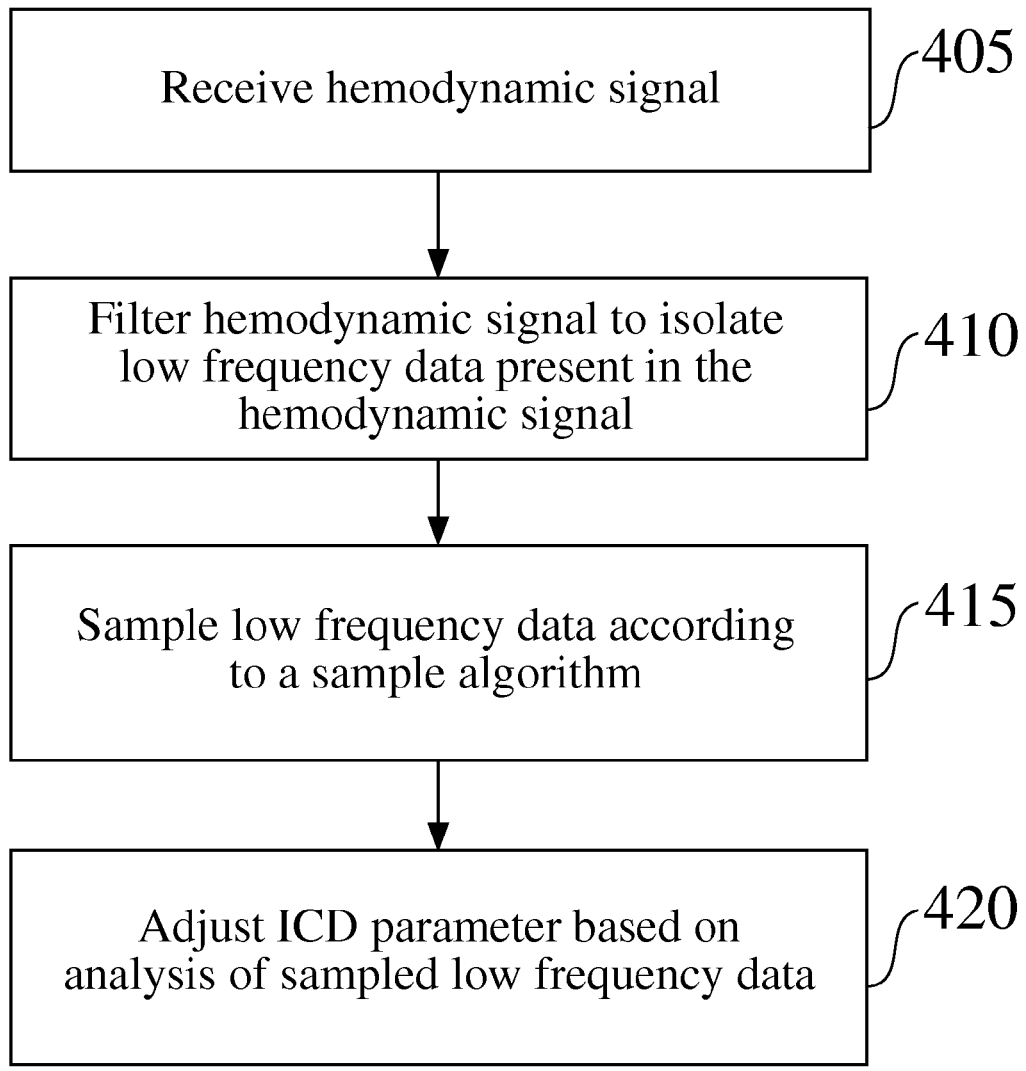
FIG. 4 is a flow chart illustrating low frequency analysis of a hemodynamic signal.

FIG. 4 is a flowchart generally describing a low frequency analysis of a hemodynamic signal. At step 405, a hemodynamic signal is received. This signal can be received at micro-controller 60, internal to the ICTD 10, or at an external device. At step 410, the hemodynamic signal is filtered to isolate low frequency data that is present in the signal. This data resides in a portion of the signal that is less than about one Hertz. Such filtering can be accomplished by a low pass filter having a cutoff frequency of about one Hertz, and can be performed in either the analog or digital domains. In step 415, this low frequency data is sampled according to a sampling algorithm. Various sampling algorithms are possible depending on the specific parameter of interest. Finally, this low frequency data is analyzed and, in one embodiment, used to adjust parameters in an ICTD 10.

Such low frequency analysis of hemodynamic signals may be used to adjust to a variety of ICTD 10 parameters. For example, low frequency analysis is beneficial for pacing interval optimization such as atrio-ventricular delay, arrhythmia therapy, lead placement for ICTDs, and pacing rate optimization. These applications are further described below. Additionally, hemodynamic signals can come from a variety of sources such as plethysmography described above, as well as other hemodynamic modalities such as blood pressure, echocardiograms, mechanical strain, heart sounds, flow noise, etc.

D. Low Frequency Analysis for Atrio-Ventricular Delay Optimization Using Plethysmography.

Conventional blood plethysmography analysis has traditionally focused on pulse amplitude, a hemodynamic variable representing blood volume. The pulse amplitude signal amplitude occupies the frequency band of approximately one to ten Hz in the blood plethysmography signal spectrum.

The present invention uses an unconventional portion of the blood plethysmography spectrum, namely about 0.03–1.0 Hz. Within this low frequency spectrum, pulse amplitude data is filtered out, leaving a hemodynamic signal that is representative of a running average of pre-capillary arteriolar volume. The benefits include a higher quality data with a simplified data analysis algorithm. In this exemplary embodiment, low frequency analysis of blood plethysmograms is used to perform atrio-ventricular delay (AV-delay) optimization.

1. Obtaining a Low Frequency Hemodynamic Signal

Figure 5:
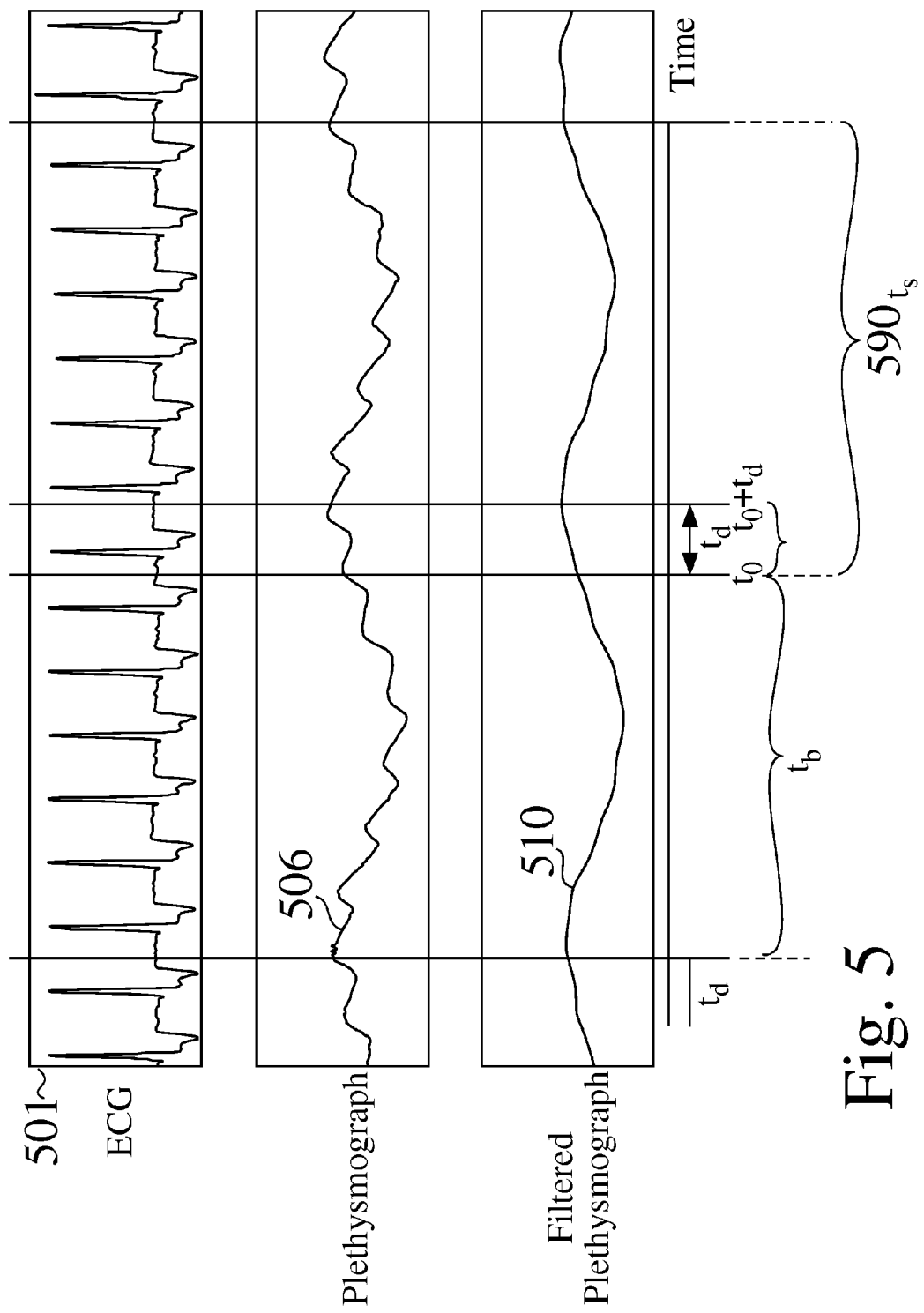
FIG. 5 illustrates a sample ECG signal, a blood plethysmograph signal and a filtered plethysmograph signal in accordance with an embodiment of the present invention.

Low frequency information from a blood plethysmography signal is obtained according to the flow chart of FIG. 4. In the present embodiment, the hemodynamic signal received according to step 405 is a blood plethysmography signal 506, as depicted in FIG. 5. According to step 410, blood plethysmography signal 506 is filtered to isolate low frequency data. One skilled in the art could accomplish this filtering in a variety of ways. One way is to use a simple low pass filter having a cutoff frequency of, in one embodiment, approximately 1.0 Hz, thus yielding a filtered signal with a frequency content of approximately 0 to 1.0 Hz. Such a filtered signal 510 is also depicted in FIG. 5. Next, according to step 415, the low frequency data is sampled according to a sampling algorithm. This procedure, which eliminates frequencies below about 0.1 Hz, is described below.

2. Sampling the Low Frequency Data

Figure 6:
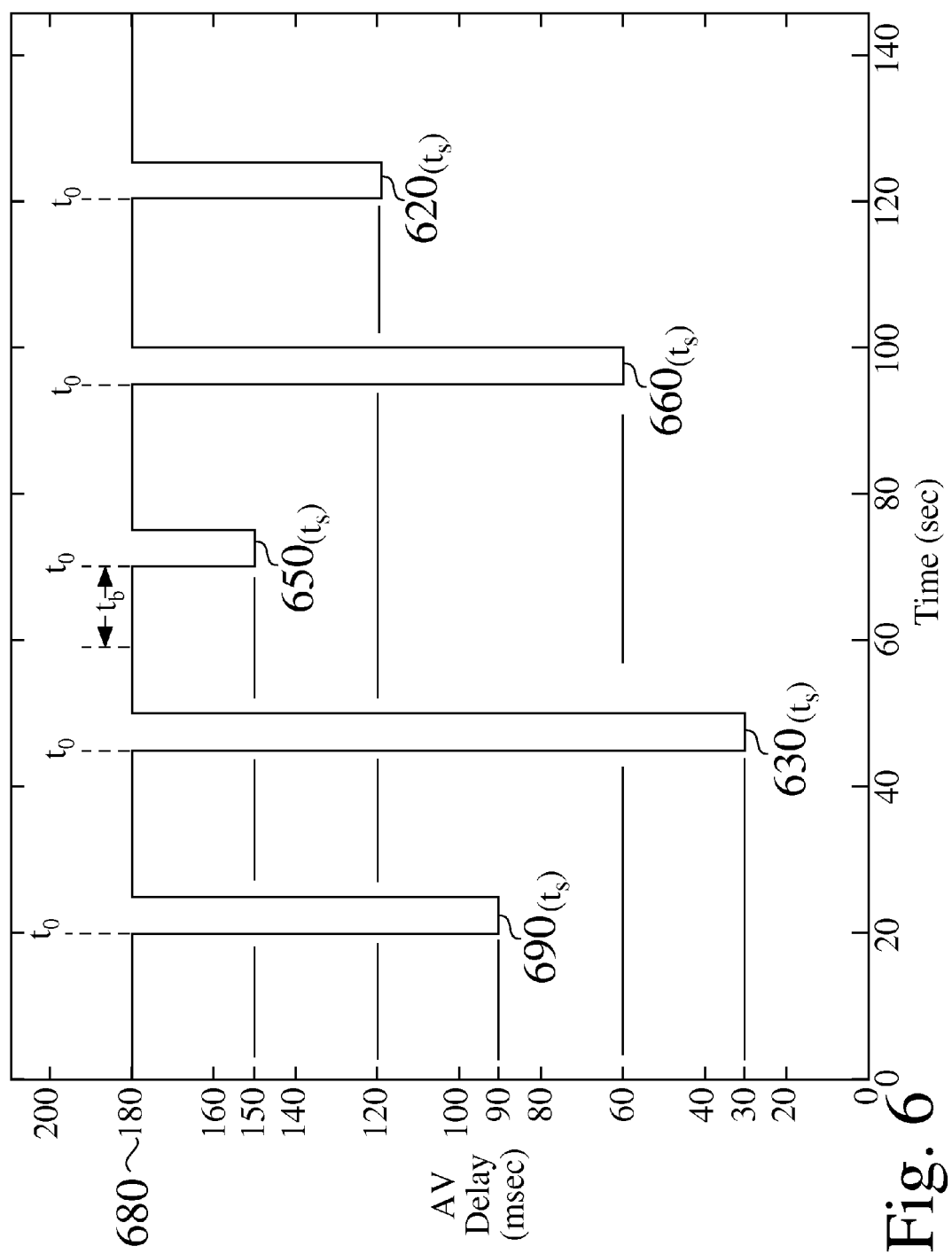
FIG. 6 is a graph illustrating the sampling algorithm of the present invention.

FIG. 6 graphically represents an exemplary sampling algorithm used in the low frequency analysis of filtered plethysmogram 510. The Y-axis represents the atrio-ventricular delay (AV-delay) in milliseconds, and the X-axis represents elapsed time in seconds as the sampling algorithm proceeds. A baseline AV delay 680, at which the sampling algorithm starts, is a predetermined AV delay. One skilled in the art could select an appropriate baseline delay to efficiently use the sampling algorithm. The baseline AV-delay 680 in this example is 180 ms, though in the preferred embodiment a baseline value closer to the expected optimum would be used. Specific baseline values in the preferred embodiment are 150 ms, for atrial sense/ventricular pace mode, and 170 ms for atrial pace/ventricular pace mode. As the exemplary sampling algorithm progresses, five excursions are made to different sample AV-delay values 690, 630, 650, 660 and 620. Each sample is a five second long excursion ($t_s$) and is made at time ($t_0$) from baseline 680. Five seconds roughly corresponds to one respiratory cycle in the subject under study, however, the invention is not limited to this excursion time. Samples 690, 630, 650, 660 and 620 typically occur after a regular interval at baseline 680 (approximately 20 seconds in this example), and are made to predetermined sample AV-delay values. For example, sample 690 is made to a sample value of 90 ms, sample 630 is made to a sample value of 30 ms, sample 650 is made to 150 ms, sample 660 is made to 60 ms, and sample 620 is made to 120 ms. This sampling algorithm is repeated to obtain three sets of representative data sets for each of the five sample AV-delay values 690, 630, 650, 660 and 620.

The sampling algorithm of FIG. 6 may be further explained by again referencing FIG. 5. In FIG. 5, electrocardiogram 501 is shown in the uppermost graph for reference. Plethysmograph signal 506 is shown in the middle graph as it varies over time. Filtered plethysmograph 510 represents blood plethysmograph data after it has passed through a low pass filter with a cutoff frequency of about one Hz. As demonstrated by signal 510, the pulse amplitude data, which occurs between about one and ten Hz, has been filtered out of the original signal 506. Realistically, useful data could be obtained at frequencies as low as about 0.03 Hz, or 30 seconds. Beyond about 30 seconds, intrinsic variability in vascular tone comes into play that adds practical problems to data analysis. Furthermore, extending analysis to frequencies below about 0.1 Hz requires extending the duration of sampled data beyond 10 seconds. Since it is desirable to perform data collection, analysis, and optimization as rapidly as possible, in the preferred embodiment the analysis is based on the portion of the hemodynamic signal corresponding to the frequency range of approximately 0.1 to 1.0 Hz. Data for the low frequency analysis is taken from filtered plethysmogram signal 510 as discussed next.

Figure 9:
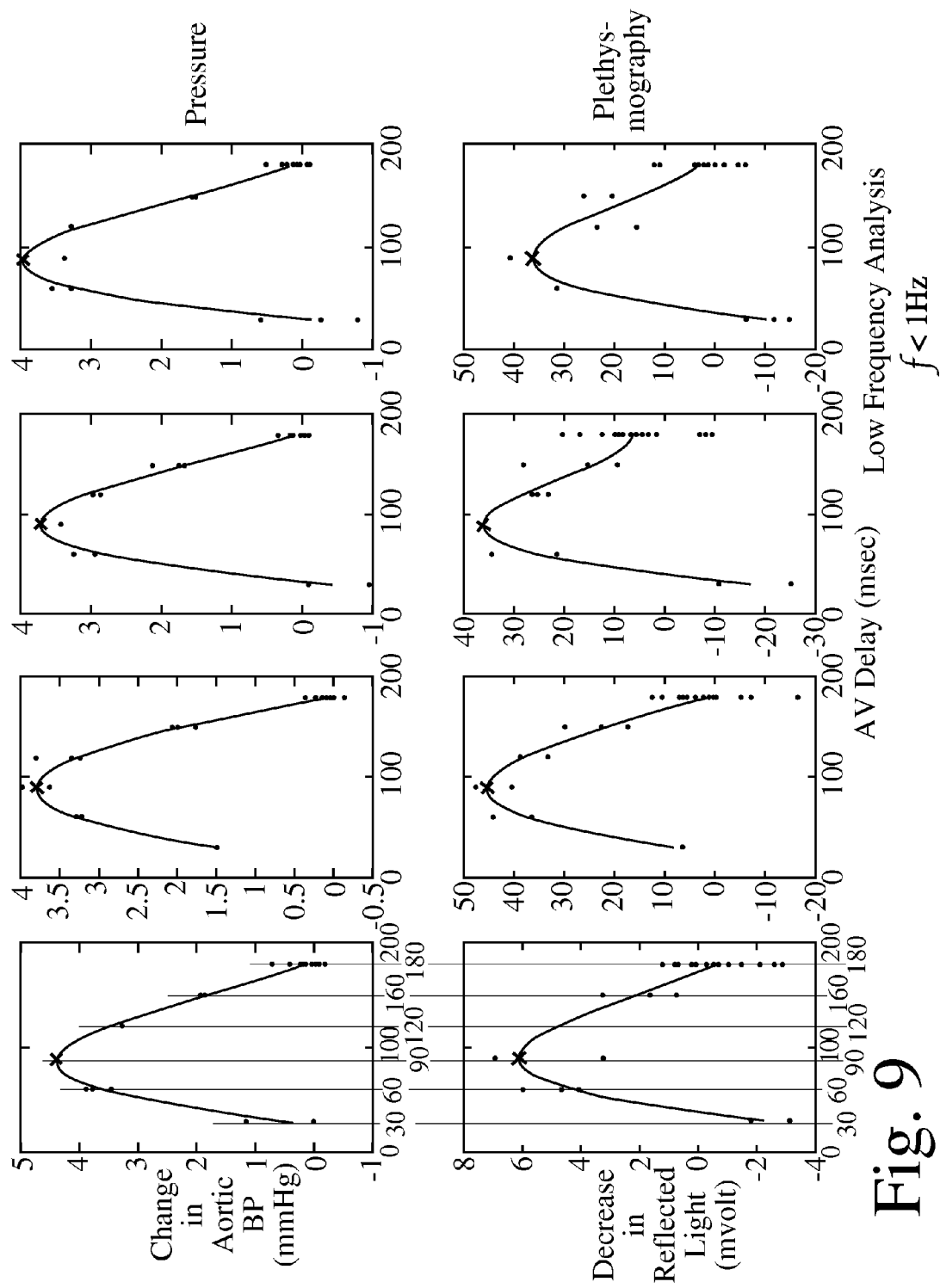
FIG. 9 illustrates low frequency analysis of both pressure data and plethysmography data.

Data is averaged over two time periods, one at baseline and one at the sample AV-delay value. For example, time period ($t_b$) represents a period of time at baseline 680. Time period ($t_s$) represents a period of time at an AV-delay sample value, for example AV-delay value 690, depicted in FIG. 6. Such exemplary sample excursions from the baseline AV-delay value 680 correspond to roughly one respiratory period. Time period $t_d$ represents a delay period where data is not collected in order to eliminate transient signal data. In this example, ($t_d$) is approximately one second. According to the present invention, the data over the time period at baseline AV-delay ($t_b$) is averaged (Ab). Similarly, the data over time period at sample AV-delay value ($t_s$) is averaged (As). The data point for given AV-delay value (e.g., sample value 690), which is plotted FIG. 9, is the difference between these two averages (Ab–As). Data for AV-delay values 630, 650, 660 and 620 are obtained in a similar fashion.

Figure 7:
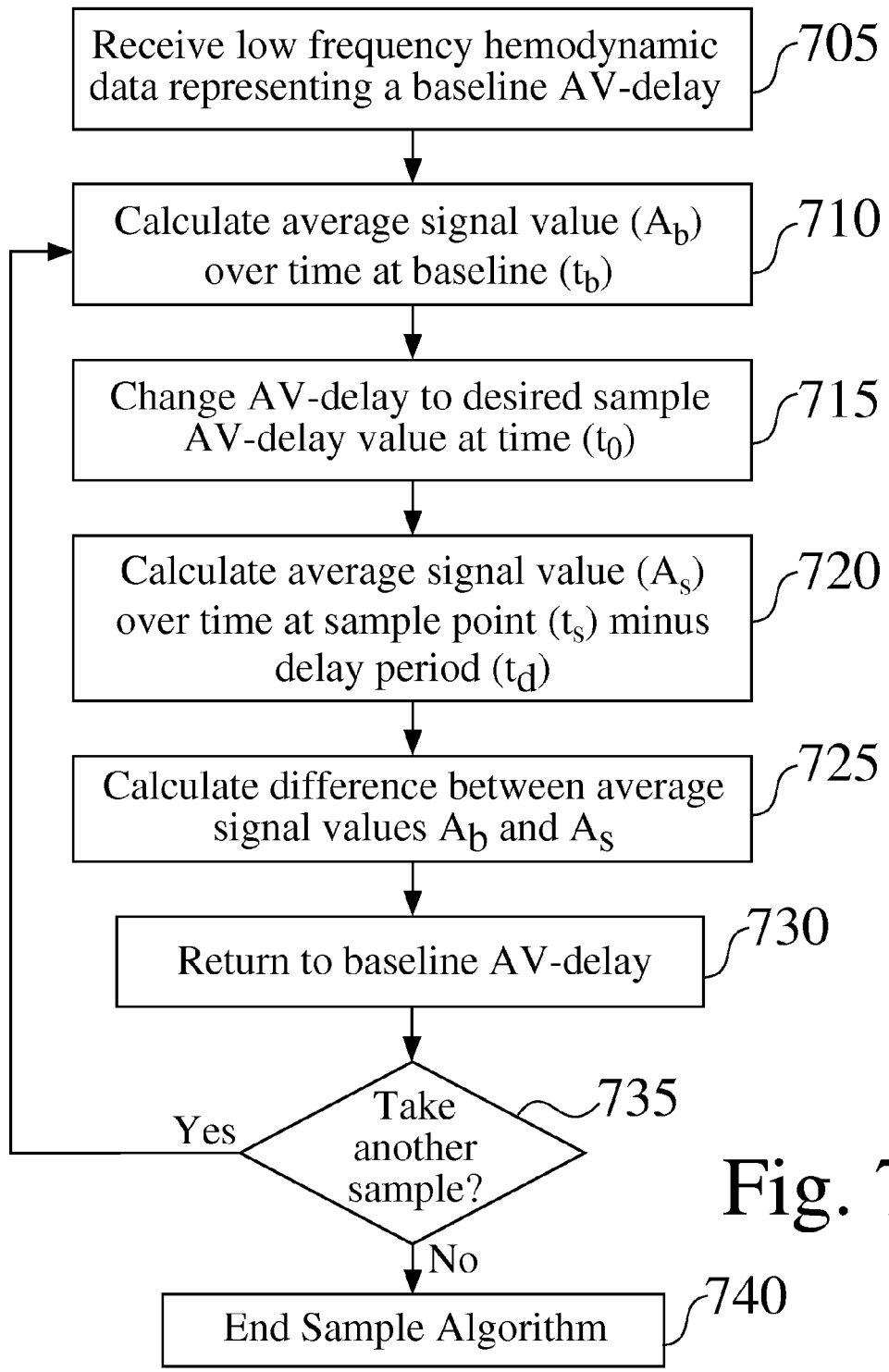
FIG. 7 is a flow chart illustrating a sampling algorithm for one embodiment of the present invention.

FIG. 7 is a flow chart illustrating the above described sampling algorithm. At step 705, low frequency hemodynamic data representing a baseline AV-delay is received. In one example embodiment, a baseline AV-delay 680 of 180 ms is used. One skilled in the art would be able to choose other appropriate baseline delays to efficiently use the sampling algorithm. At step 710, the average value of the signal (Ab) over the time spent at baseline value ($t_b$) is calculated. Next, at step 715, the AV delay is changed to a desired sample AV-delay value at time ($t_0$). At step 720, the average signal value (As) over the time spent at the AV-delay sample value ($t_s$) minus the delay period ($t_d$) is calculated. At step 725, the difference between average signal values (Ab) and (As) is calculated. This difference becomes one data point in the overall low frequency data analysis displayed in FIG. 9. Next, at step 730, the sampling algorithm returns to the predetermined baseline AV-delay. Finally, at step 735, if another sample is to be taken, the sampling algorithm returns to step 710. If no more samples are to be taken, the sampling algorithm ends according to step 740.

It should be noted, in this example, that the length of time over which the data is averaged at the baseline ($t_b$) may vary. In one embodiment, this time is equal to the time spent at the sample value ($t_s$). This, however, is not required as averages over greater or less time periods would yield acceptable results. However, it is preferable that the averages be over corresponding regions of the respiratory cycle.

It is important to note that order in which the data analysis occurs is flexible. For instance, it is not important which averages are calculated first. Additionally, processing can be done in either the analog domain or digital domain. While optimization of AV delay was illustrated here, the same technique can be used to optimize inter-ventricular interval, or in general, any inter- or intra-chamber pacing interval.

2. Data Analysis

Referring back to FIG. 1, data analysis may be accomplished by microcontroller 60 of the ICTD described above.

Figure 8:
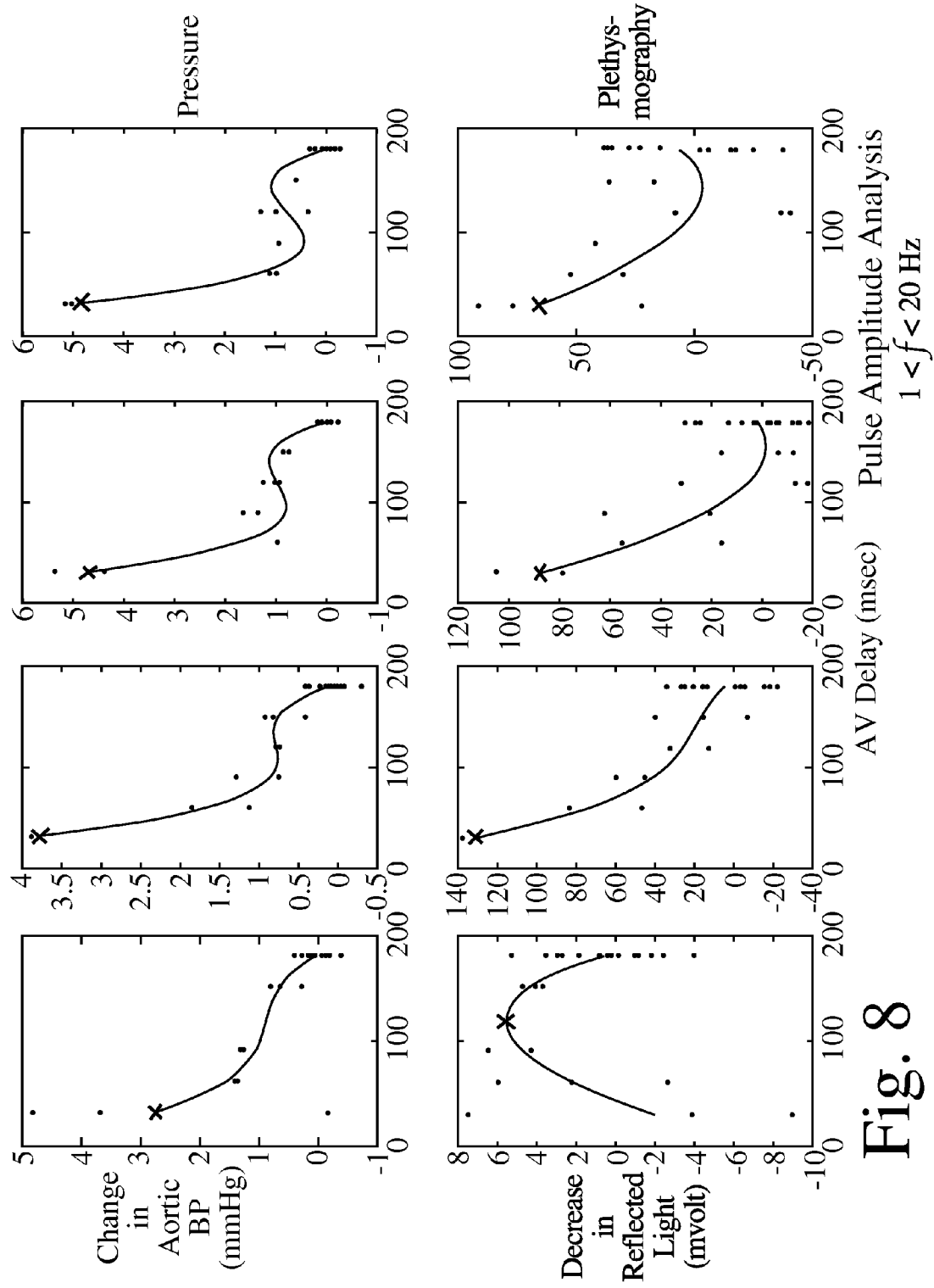
FIG. 8 illustrates pulse amplitude analysis at conventional frequencies of both pressure data and plethysmography data.

Alternatively, data analysis may be accomplished externally to the ICTD. The results of the optimization may then be programmed into the ICTD via telemetry circuit 100. FIG. 8 illustrates examples of AV-delay curves obtained from conventional pulse amplitude analysis of a hemodynamic signal. FIG. 9 illustrates the result of low frequency analysis of two hemodynamic signals according to the present invention. For both modes of analysis, change in aortic pressure and decrease in reflected light are plotted as a function of AV-delay. The upper panels represent pressure data. The lower panels represent the plethysmography data. Vertically aligned panels show data obtained from the same run. Solid lines show the best fitting $3^{rd}$ degree polynomial to the data (dots), and 'x' marks the maximum value of the polynomial. The location of the 'x' on the AV-delay axis represents the optimal AV-delay predicted by the technique. In the present example, three sets of data were collected for each of the four runs. As can be seen, there are three data points for each excursion value. There are 15 data points at the baseline value of 180 ms, which correspond to the returns to baseline following each of the five excursions for each of the three data sets (5×3=15).

An upside-down U curve is expected for this data and would represent the expected poor performance at extremely long or short atrio-ventricular delays, with better performance at intermediate delays. A maximum occurring at an extremely long or short AV delay, as frequently occurs with pulse amplitude analysis (FIG. 8) indicates a failure in the estimation technique. The quality of the data can be quantitatively expressed as the ratio of the difference between the maximum of the polynomial and the baseline value, to the standard deviation of the hemodynamic variable (e.g., pressure or plethysmography in this example). Results in which the maximum of the polynomial occurs at an extreme (short or long) AV delay are assigned a Q less than one. The quality of the AV-curves for both conventional pulse amplitude analysis, and low frequency analysis is reflected below in Table 1. A higher quality number indicates more accurate data.

TABLE 1

QUALITY(Q)

| Data file | cutoff freq | Low Frequency Analysis Quality | | Pulse Amplitude Analysis Quality | |
|---|---|---|---|---|---|
| | | Pressure | Pleth | Pressure | Pleth |
| L1062702.a16 | f < 1 Hz | 19.2079 | 5.3301 | | |
| | f < 20 Hz | 3.9285 | 4.7973 | | |
| | 1 < f < 20 Hz | <1 | <1 | <1 | <1 |
| L1062702.a18 | f < 1 Hz | 27.6602 | 5.9949 | | |
| | f < 20 Hz | 4.1935 | 6.1015 | | |
| | 1 < f < 20 Hz | <1 | <1 | <1 | <1 |
| L1062702.a20 | f < 1 Hz | 26.0859 | 3.3635 | | |
| | f < 20 Hz | 3.1654 | 2.978 | | |
| | 1 < f < 20 Hz | <1 | <1 | <1 | <1 |
| L1062702.a22 | f < 1 Hz | 25.8398 | 6.3727 | | |
| | f < 20 Hz | 3.4331 | 6.2319 | | |
| | 1 < f < 20 Hz | <1 | <1 | <1 | <1 |

FIG. 8 represents conventional pulse amplitude analysis at frequencies between one and twenty Hz. The data points are obtained using the sampling algorithm described above for both pressure and plethysmography data, except that instead of plotting the average data obtained from a low pass filtered signal (as contemplated by the present invention), the data represents traditional pulse amplitude analysis. The curves generally do not have the expected 'upside-down U' shape for hemodynamic response as a function of AV-delay. Moreover, as shown in Table 1, none of the curves in FIG. 8 achieve a Q value greater than one. Though pulse amplitude analysis does suggest the expected functional form for one data set (lower left panel in FIG. 8), the low frequency analysis, described below, is consistently and dramatically superior.

According to the present invention, the low frequency portion of the plethysmograph (f<1.0 Hz in this example) reflects average pre-capillary arteriolar volume. This is because acute changes in mean arterial blood pressure cause corresponding changes in the arteriolar volume. Changing the AV-delay to a less effective interval (e.g., from 150 ms to 30 ms), causes an acute decrease in mean arterial pressure, and a corresponding reduction in average arteriolar volume. For the plethysmography signal, this means that less light is absorbed in the tissue, and an increased amount of light is detected at the photodiode. In the present example, the time scale over which these changes occur is about 1–2 seconds on the short end (approximately one Hz), to about 5–10 seconds on the long end (approximately 0.1–0.2 Hz).

FIG. 9 represents data from the low frequency analysis as envisioned by the present invention. Data points are obtained according to the sampling algorithm described above and plotted for each of the four runs. The low frequency results shown in FIG. 9 are clearly superior to the pulse amplitude curves in FIG. 8. As can be seen, the curves resulting from the low frequency analysis demonstrate the expected upside down U shape. Additionally, Table 1 demonstrates the increased quality produced by the low frequency data. For example, for the low frequency plethysmography data, where the cutoff frequency includes the low frequency portion of the plethysmography signal (below about one Hz), the data quality is markedly superior to the results that do not include the low frequency portion of the signal. Indeed, the quality of the data where the low frequency information is excluded does not exceed one for any of the four runs.

The data is even more persuasive for the pressure data. As with the plethysmography data, where the signal excludes low frequency information, the data quality does not exceed one. Where the entire frequency spectrum below 20 Hz is included, the data quality is between approximately 3 and 4.2. Where information above about one Hz is excluded, the quality jumps to between 19 and 28. This is because the pulse amplitude information (occurring above 1 Hz) acts as noise in this analysis, so that excluding it improves the calculated AV delay curves.

In sum, Table 1 clearly indicates that, for both the pressure and plethysmography signals, the most valuable information for optimization of AV-delay lies in the frequency range below about one Hz. For conventional pulse amplitude analysis, where the information lies between one and twenty Hz, the quality of data never exceeds one.

E. Other Applications of Low Frequency Analysis

As noted above, low frequency analysis of hemodynamic signals such as pressure and plethysmography is not limited to AV-delay. It is useful for optimizing other parameters as well. For example, the low frequency analysis of the present invention is useful for targeted arrhythmia therapy, ICD lead placement, and pacing rate cutoff.

1. Arrhythmia Therapy

In conventional implantable cardioverter defibrillators, the electrical activity of the heart is continuously monitored for evidence of dangerous arrhythmias. Ventricular fibrillation (VF) is the most lethal. It always results in a severe loss of blood pressure, and if not terminated rapidly will quickly lead to death. Because of this, when it is detected the ICD quickly delivers a high-energy shock to the heart with the goal of terminating the VF arrhythmia.

VF is generally detected reliably by electrical sensing, however, the detection and therapy of other types of arrhythmias are not always as straightforward. Ventricular tachycardia (VT) can lead to hemodynamic compromise associated with reduced blood pressure and perfusion of vital organs, and in fact it is not uncommon for VT to degenerate to VF. For these types of VT it is also desirable to rapidly and aggressively deliver high energy electrical therapy. In other cases, however, VT may spontaneously self terminate, or it remain hemodynamically stable and support adequate blood pressure and perfusion. In these cases a less aggressive form of therapy such as anti-tachycardia pacing (ATP) is appropriate. ATP is desirable because, in contrast to high-energy defibrillation shocks, it is painless for the patient and conserves battery power.

Though some information, such as heart rate and patient history, is available that aids the device in determining whether ATP or high-energy shock should be used, the reliability of the ICD in making this determination can be limited. Incorporating feedback from a hemodynamic sensor into the therapy decision algorithm of the device allows the device to better deliver the high-energy therapy during episodes of potentially lethal arrhythmias, and deliver the low-energy ATP during episodes of the less dangerous, hemodynamically stable arrhythmias.

The situation is further complicated by the frequent occurrence of arrhythmias that originate in the atria. ICD manufacturers have developed electrogram analysis algorithms that are intended to detect whether the arrhythmia is of ventricular origin, such as VT, or is of atrial origin, such as atrial fibrillation (AF) or atrial flutter (AFl). It is generally seen as desirable to avoid delivering high-voltage therapy for AF and AFl, however, the ability of electrogram-analysis algorithms to distinguish these from VT is not perfect. Furthermore, for patients with compromised cardiac function it may be that AF and AFl are hemodynamically unstable. For these patients some physicians will program the ICD to deliver high-energy therapy for relatively low heart rates, with the intention of terminating any arrhythmia (VT, AF, AFl) that may occur. Feedback from a hemodynamic sensor would greatly improve the accuracy of the ICD in distinguishing between hemodynamically stable and unstable atrial arrhythmias.

Figure 10:
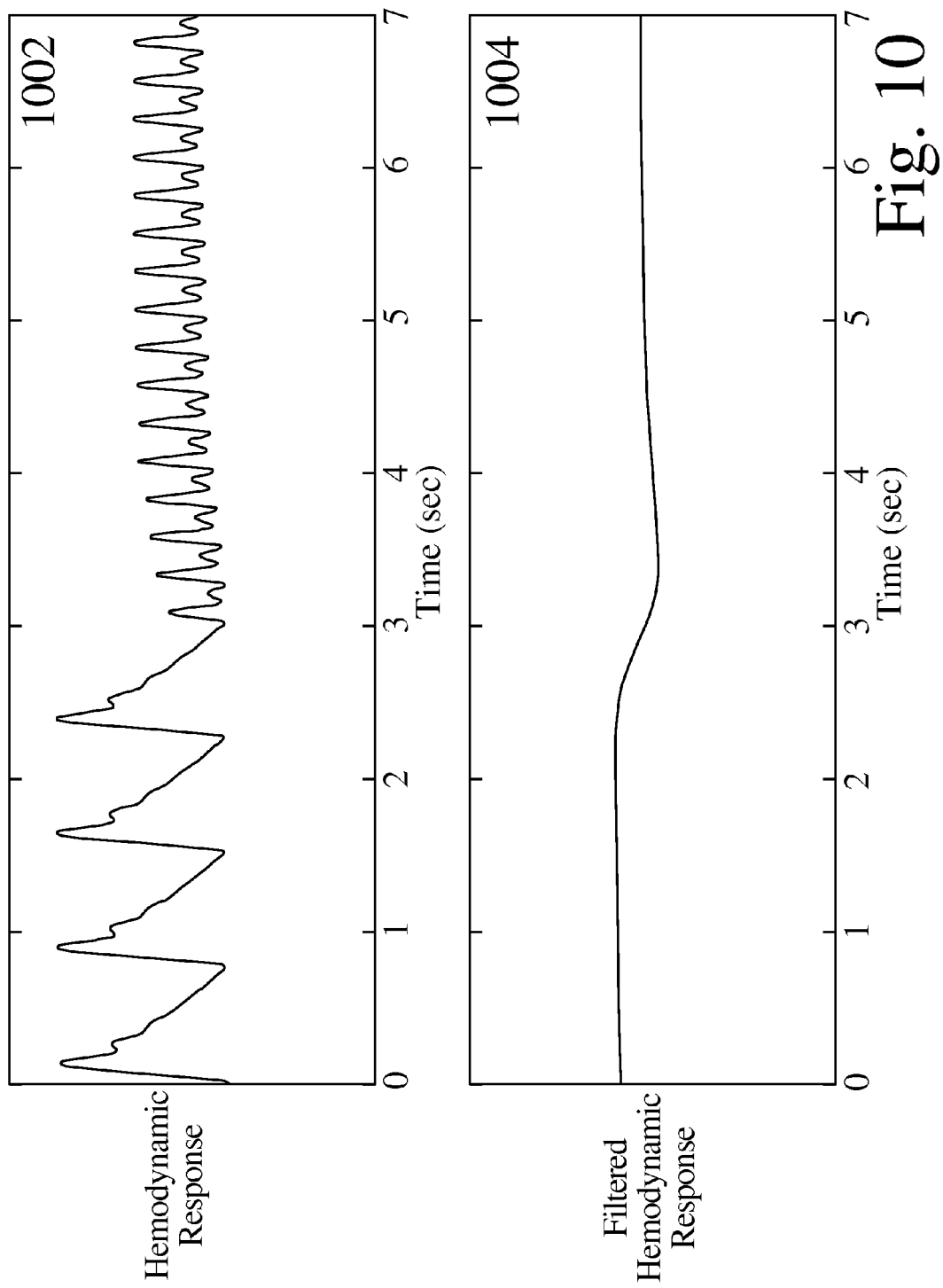
FIG. 10 illustrates the onset of a hemodynamically stable atrial arrhythmia.

The role of low-frequency analysis in this context is illustrated using computer simulation in FIGS. 10 and 11. FIG. 10 illustrates the onset of a hemodynamically stable atrial arrhythmia. Graph 1002 illustrates the signal from a hemodynamic sensor such as a photoplethysmography or arterial pressure transducer. Graph 1004 presents the low-frequency content of the sensor output. Initially (Time <3 sec), a robust pulse and moderate average pressure is seen, consistent with normal sinus rhythm. At three seconds the heart rate increases from 75 to 225. While the pulse amplitude decreases significantly, the average response decreases only slightly, consistent with a hemodynamically stable VT or hemodynamically stable atrial arrhythmias. Using the hemodynamic sensor and low frequency analysis, the ICD would appropriately withhold high-energy therapy, and instead attempt to terminate the arrhythmia with low-energy ATP.

FIG. 11 illustrates the onset of a hemodynamically unstable arrhythmia, such as unstable VT, or AF or AFl in a patient with compromised cardiac function. As before, the heart rate increases from 75 to 225, but in this case both the pulse amplitude and the average hemodynamic response are greatly attenuated. Incorporating the low frequency hemodynamic response information into its detection and therapy algorithm would allow the ICD to deliver a high-energy shock, and greatly increase the likelihood of terminating the unstable arrhythmia.

Conventional pulse amplitude analysis alone, independent of the low-frequency hemodynamic response information, can provide useful information in the detection and treatment of unstable arrhythmias. However, analysis that incorporates low-frequency information has several advantages. First, it is the mean arterial pressure (MAP), not the pressure pulse amplitude, that most directly reflects how successfully perfusion is occurring. Low-frequency analysis of hemodynamic data, whether pressure, plethysmographic, or flow, allows the device to act according to the perfusion status of the patient. It is this, rather than heart rate or arrhythmia locus, that is central to determining the most appropriate therapy. Second, the low frequency region of the hemodynamic signal spectrum is less sensitive to likely sources of noise or motion artifact, such as the changes in posture or chest compressions that may accompany the onset of an arrhythmia. In sum, low frequency analysis confers advantages not available in conventional pulse amplitude analysis.

2. ICD Lead Placement

Heart failure is a multi-faceted clinical syndrome that is centered on the inability of the heart to meet the perfusion requirements of the body. It typically includes systolic and/or diastolic dysfunction, neurohumoral abnormalities, and cellular and anatomical remodeling of the heart. Regardless of the etiology, heart failure patients commonly develop marked dilation of the chambers of the heart, particularly the left ventricle (LV), resulting in delayed or aberrant electrical conduction and mechanically dyssynchronous and inefficient contractions. Recent studies have demonstrated that pacing in both the right and the left ventricle improves cardiac synchrony, work efficiency, and clinical outcomes. The biventricular pacing configuration used in cardiac resynchronization therapy (CRT) is in contrast to the conventional approach to pacing, in which the right ventricle is stimulated, but not the left.

It is known that the effectiveness of CRT depends on the particular placement of the LV pacing lead, with some sites within the LV yielding more effective resynchronization than others. The ability to quickly and conveniently compare the effectiveness of two or more candidate lead placements would facilitate optimizing therapy for the individual patient.

It would be desirable to use feedback from a hemodynamic sensor to perform a quantitative comparison of the effectiveness of different candidate placements. Photoplethysmography and arterial pressure are convenient sensor modalities. A photoplethysmography signal can be obtained with a simple finger tip sensor, such as those used in pulse oximetry, or by using a subcutaneous sensor, either standalone or incorporated into the device being implanted. Arterial pressure is obtained as part of the implant procedure, often using an intra-arterial catheter which provides high-quality, continuous data. Other hemodyanmic sensors are possible, such as cardiac output or stroke volume measured using echocardiography, though this approach requires special technical expertise, and would be difficult to integrate into the clinical setting of ICD or pacemaker implant. Moreover, it does not provide real-time quantitative information.

Figure 12A:
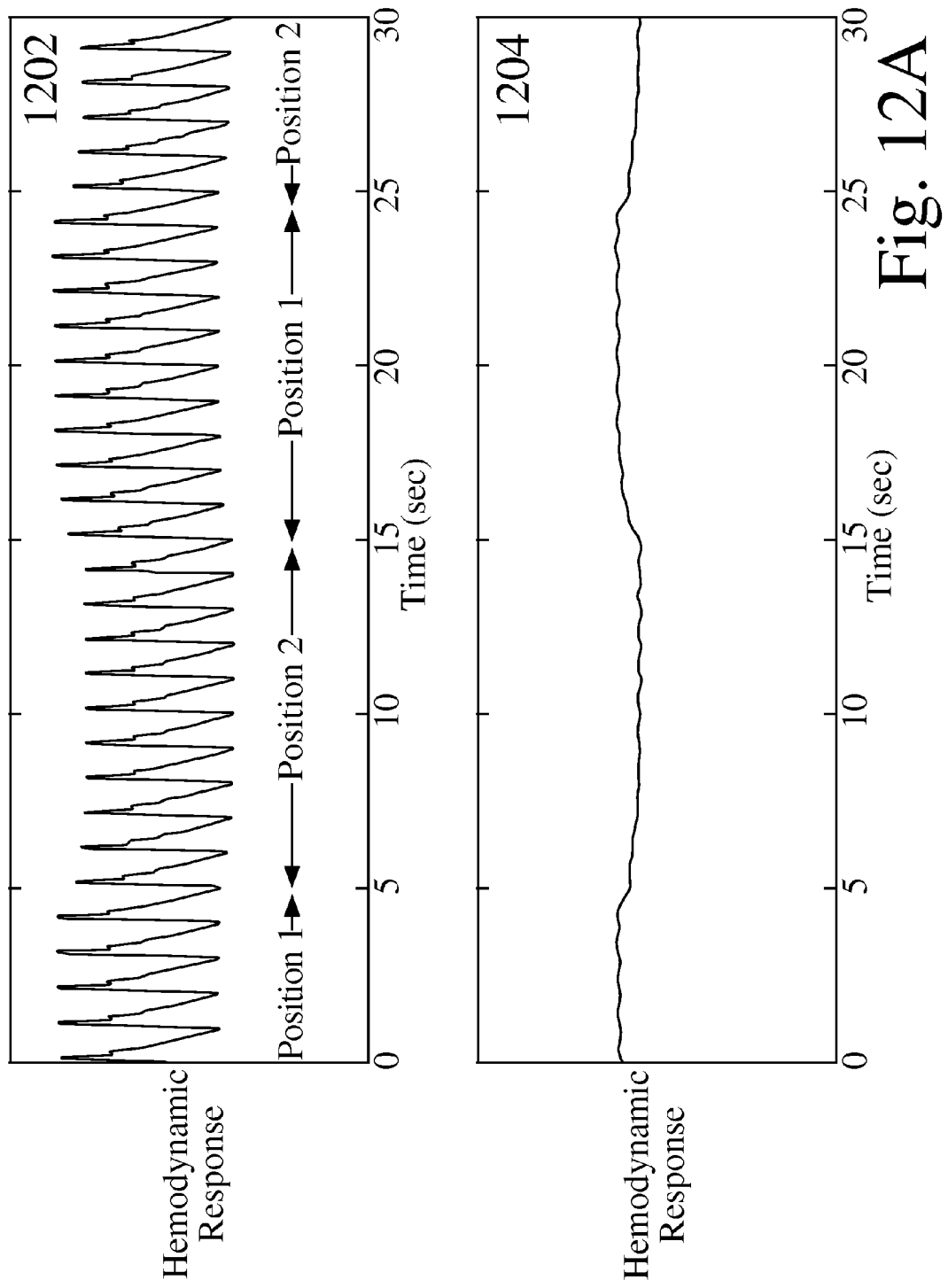
FIG. 12A illustrates the effect of various ICD lead placements for both pulse amplitude and low frequency analysis.

With real-time, quantitative hemodynamic information available candidate lead placements can be directly compared for effectiveness. For example, the sensor output could be recorded while alternating between two different LV pacing sites, as illustrated with computer simulation in FIG. 12A.

Graph 1202 illustrates conventional pulse amplitude data for two different lead placements. Graph 1204 illustrates the filtered, low frequency information carried in the pulse amplitude data stream. In this example the difference between the two sample sites is readily apparent, however, in a real setting noise and intrinsic variability, such as that due to respiration, would make visual assessment more difficult, particularly in the unfiltered data. Furthermore, the differences between candidate pacing sites are likely to be quite subtle, requiring quantitative analysis to reliably detect. The low frequency analysis is less susceptible to such noise and intrinsic variability. Furthermore, comparisons can be repeated multiple times, which allows averaging that further minimizes noise and variability. Such analysis using the low frequency data confers benefits not available in the conventional pulse amplitude analysis, although the invention is not limited to low frequency analysis.

Figure 12B:
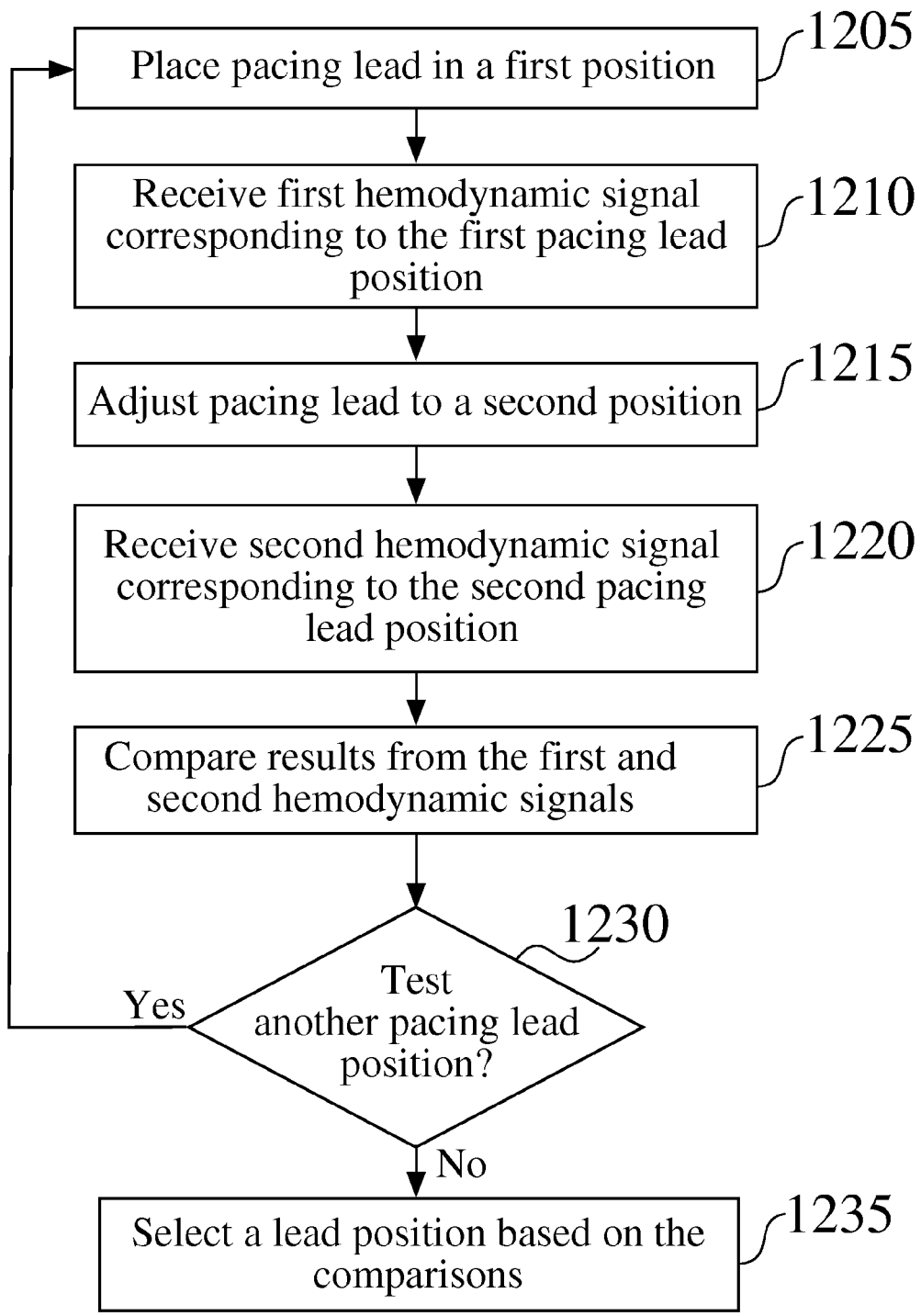
FIG. 12B illustrates a method for using hemodynamic feedback to optimize ICD lead placement.

FIG. 12B illustrates a method for using hemodynamic feedback to optimize ICD lead placement. In step 1205, the pacing lead is placed in a first position. In step 1210, a first hemodynamic signal is received that is representative of the first pacing lead position. In step 1215, the pacing lead is adjusted to a second position. Or, if multiple selectable electrodes are present on a single lead, the lead is not physically repositioned, rather, a different pacing electrode is selected, causing a different site to be paced. In step 1220, a second hemodynamic signal is received that is representative of the second pacing lead position. In step 1225, the two hemodynamic signals are quantitatively compared to each other. If another pacing lead or pacing site is to be tested, then steps 1205 through 1225 are repeated, according to step 1230. Based on these multiple comparisons, as indicated at step 1235, a person skilled in the art can then use the comparative results to optimize the pacing lead position.

3. Pacing Rate Cutoff

Modern pacemakers and ICDs can adaptively change the heart pacing rate to accommodate the metabolic needs of the patient. However, the prediction of optimum pacing rate is at present based on surrogates for metabolic demand, such as physical motion and respiration. The pacemaker has no means of verifying that the pacing rate it's delivering is actually beneficial to the patient.

For normal subjects, increasing the heart rate will increase the cardiac output, as long as the heart rate remains within the normal physiologic range. For patients with compromised ventricular function, however, even moderately elevated pacing rates, such as 90 beats per minute, can lead to a decrease in cardiac output. Because of this, rate-adaptive pacemakers typically allow the physician to program an upper rate limit that the pacemaker will not exceed. Based on experience and intuition, the physician estimates the appropriate cutoff based on the patient's clinical condition and history. The time and financial costs of quantitatively determining the optimal cutoff rate for each patient would be substantial, and the accuracy of the result would be questionable since this parameter is likely to be sensitive to changes in fluid status, disease state, and numerous other factors. Because of this, the determination made by the physician remains an estimate rather than a rigorously and quantitatively determined parameter. Incorporating hemodynamic information into this analysis would allow the pacemaker to briefly test higher pacing rates to determine the point at which higher rates start to compromise cardiac output.

Figure 13A:
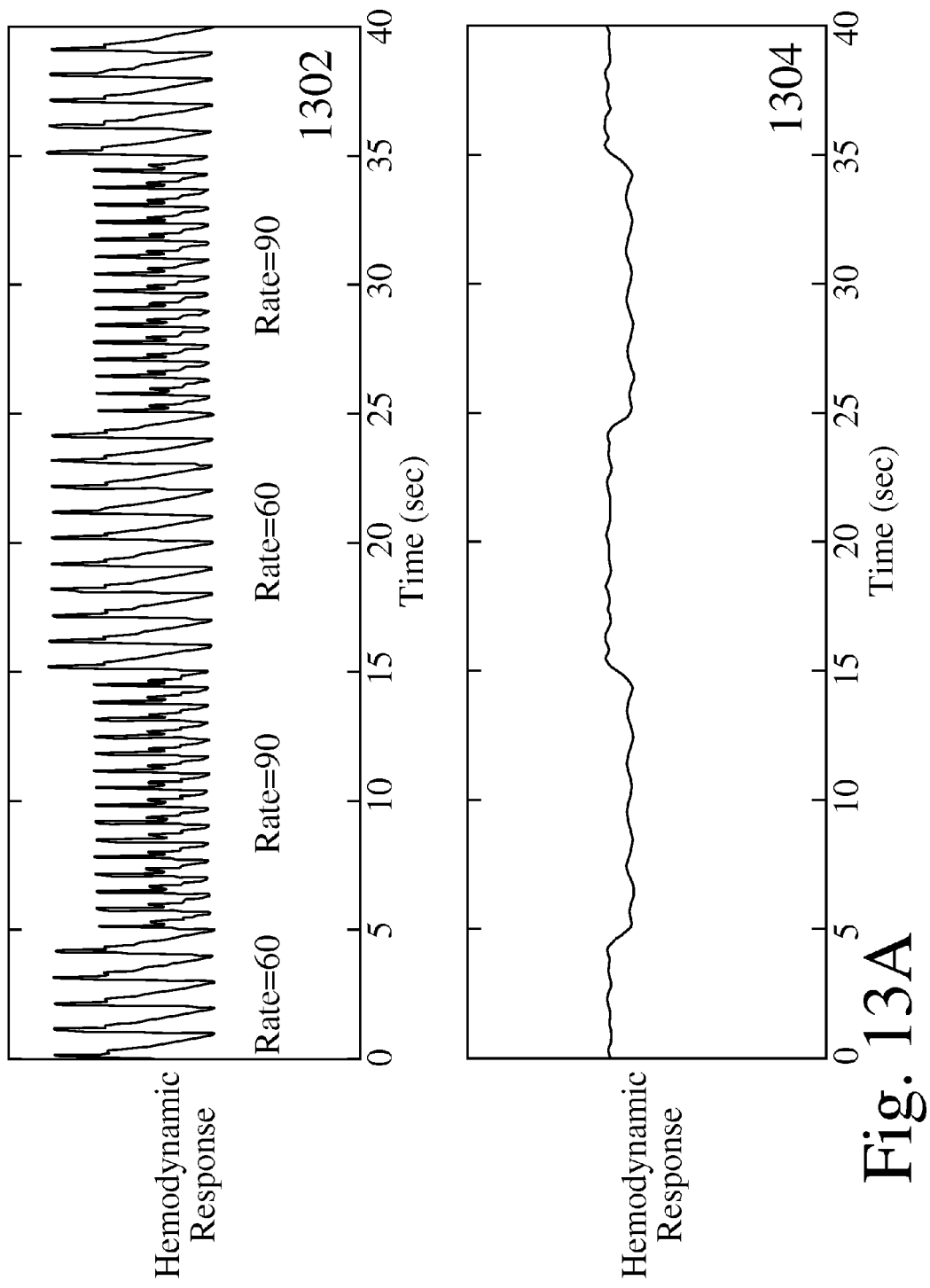
FIG. 13A illustrates the effect of various pacing rate cutoff values for both pulse amplitude and low frequency analysis.

This concept is illustrated using computer simulation in FIG. 13A. Graph 1302 represents the conventional unfiltered data, while graph 1304 represents the low-pass filtered data, in which the effect of changing from a baseline pacing rate of 60 to a moderately high rate of 90 is shown. For a normal subject one would expect an acute increase in blood pressure and blood pressure correlates, such as photoplethysmography, when the pacing rate is acutely increased. In this illustration, however, both the pulse amplitude and the average value decrease acutely after the increase in pacing rate, consistent with the pattern that sometimes occurs in patients with compromised cardiac function when the pacing rate is increased.

Basing the analysis on the low-pass filtered version of the signal 1304 facilitates analysis by providing greater immunity to noise and intrinsic physiologic variability. By repeatedly performing multiple pair-wise comparisons of different rates, the device can determine the rate level at which the pumping ability of the heart begins to decrease.

This embodiment of the invention, however, is not limited to low frequency analysis. By averaging the pulse amplitude value at each pacing rate, acceptable results may be obtained. Additionally, the total blood volume is represented by the area under the signal. Thus, by integrating the signal depicted in graph 1302, blood volume changes may be obtained for each pacing rate.

Figure 13B:
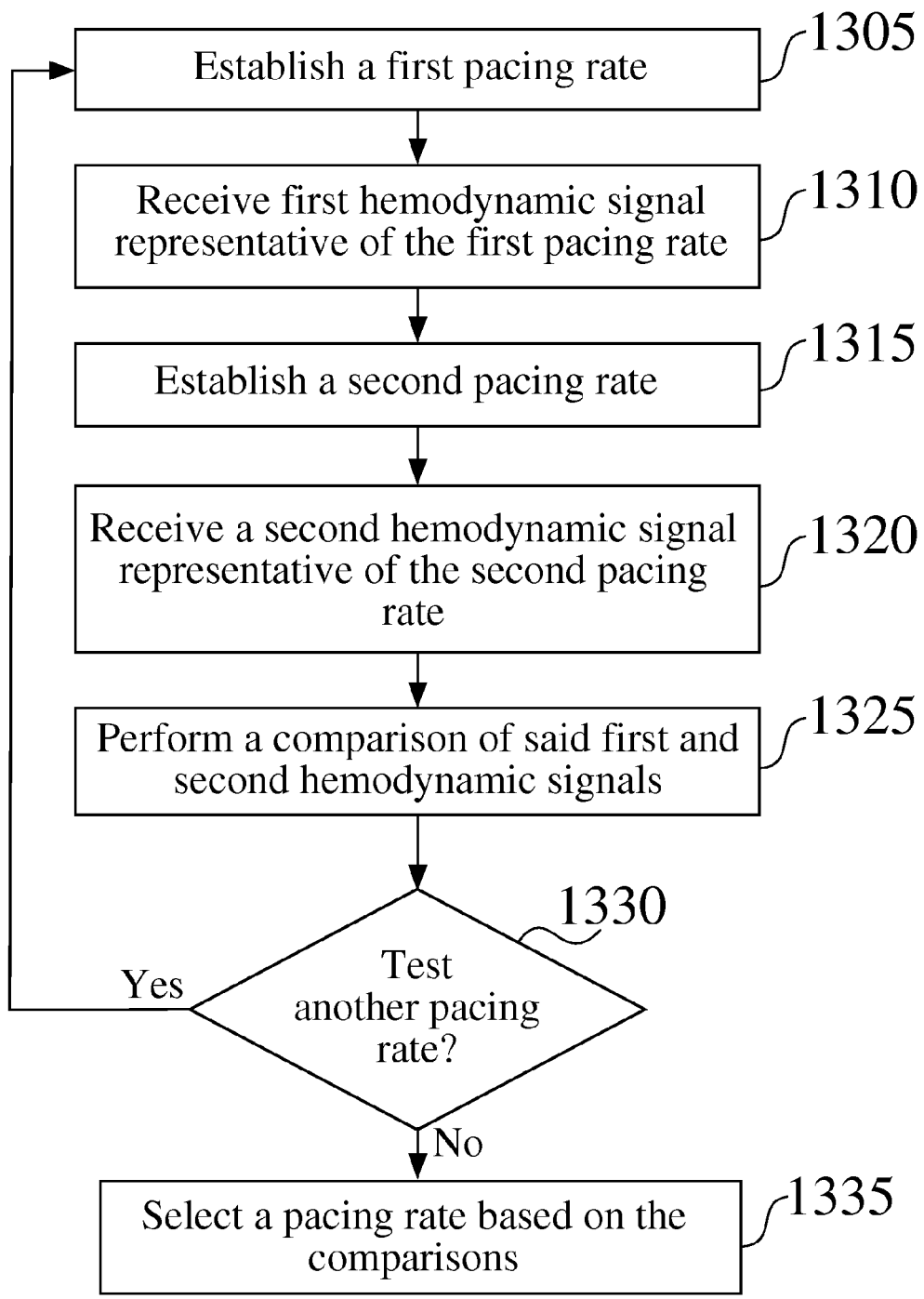
FIG. 13B illustrates a method for using hemodynamic feedback to optimize ICD pacing rate cutoff.

FIG. 13B illustrates a method for using hemodynamic feedback to optimize ICD pacing rate cutoff. In step 1305, a first pacing rate is established. In step 1310, a first hemodynamic signal is received that is representative of the first pacing rate. In step 1315, a second pacing rate is established. In step 1320, a second hemodynamic signal is received that is representative of the second pacing rate. In step 1325, the two hemodynamic signals are quantitatively compared to each other. If another pacing rate is to be tested, then steps 1305 through 1325 are repeated, according to step 1330. Based on these multiple comparisons, one skilled in the art can optimize the pacemaker or ICD pacing rate.

While the test for degradation of hemodynamic performance with increasing pacing rate was illustrated here, the same test can be used to avoid performance degradation as the rate is decreased as well. In other words, the device could automatically determine both limits (high and low) of the range of pacing rates that the patient could tolerate and thus the rate range within which the pacemaker or ICD should ideally operate. This range could be periodically and automatically tested to track changes over time, such as those due to changes in volume status, autonomic tone, and disease status.

In both the pacing rate application and the LV lead placement application, as illustrated in these figures, comparisons can be repeated multiple times to allow averaging in order to minimize the effect of noise and variability.

CONCLUSION

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A method for optimizing a parameter in an implantable cardiac therapy device (ICTD), comprising:
    (a) receiving a hemodynamic signal generated by plethysmography;
    (b) filtering said hemodynamic signal to isolate low frequency data present therein;
    (c) sampling said low frequency data according to a sample algorithm metric; and
    (d) adjusting the parameter based on an analysis of said sampled low frequency data.

2. The method of claim 1, wherein said sampling step comprises sampling said low frequency data present in a portion of a frequency spectrum of said hemodynamic signal that is less than about one Hertz (1 Hz).

3. The method of claim 2, wherein said sampling step comprises sampling said low frequency data present in a portion of a frequency spectrum of said hemodynamic signal that is between about 0.1 and about 1.0 Hz.

4. The method of claim 3, wherein said sampling step comprises sampling said low frequency data present in a portion of a frequency spectrum of said hemodynamic signal that is between about 0.03 and about 1.0 Hz.

5. An apparatus for optimizing a parameter in an implantable cardiac therapy device (ICTD), comprising:
    a photoplethysmography sensor adapted to generate a hemodynamic signal;
    means for receiving a said hemodynamic signal;
    means for isolating low frequency data present in said hemodynamic signal;
    means for sampling said low frequency data;
    means for adjusting the parameter based on an analysis of said sampled low frequency data.

6. The apparatus of claim 5, wherein said receiving means is a programmable microcontroller of the ICTD.

7. The apparatus of claim 5, wherein said isolating means is a low pass filter having a cutoff frequency of approximately one Hertz.

8. An apparatus for optimizing a parameter in an implantable cardiac therapy device (ICTD), comprising:
    means for receiving a hemodynamic signal, wherein said hemodynamic signal represents blood pressure;
    means for isolating low frequency data present in said hemodynamic signal;
    means for sampling said low frequency data;
    means for adjusting the parameter based on an analysis of said sampled low frequency data.

9. A method for optimizing atrio-ventricular (AV) delay in an implantable cardiac therapy device (ICTD), comprising:
    (a) receiving low frequency hemodynamic data representing a baseline AV-delay;
    (b) calculating a baseline average of said data representing said baseline AV-delay;
    (c) changing AV-delay to a desired sample point AV-delay;
    (d) calculating a new average of data representing said desired sample point AV-delay;
    (e) calculating a difference between said baseline average and said new average;
    (f) returning to said baseline AV delay;
    (g) repeating steps (b) through (f) for a desired number of additional sample point AV-delays, whereby step (e) produces a corresponding difference for each additional sample point AV delay; and
    (h) selecting an optimal AV-delay based on said differences.

10. The method of claim 9, wherein said low frequency hemodynamic data exists in a low frequency portion of a hemodynamic signal that is less than about one Hertz.

11. The method of claim 10, wherein said low frequency portion is between about 0.1 Hz and about 1.0 Hz.

12. The method of claim 10, wherein said low frequency portion is between about 0.03 Hz and about 1.0 Hz.

13. A method for optimizing pacing lead placement in an implantable cardiac device, comprising:
    (a) placing a pacing lead in a first position;
    (b) receiving a first hemodynamic signal corresponding to said first pacing lead position;
    (c) adjusting said pacing lead to a new position;
    (d) receiving a new hemodynamic signal corresponding to said new pacing lead position;
    (e) comparing said first and new hemodynamic signals;
    (f) repeating steps (c) through (e) until no further comparisons are desired; and
    (g) selecting a pacing lead position based on said comparisons.

14. The method of claim 13, wherein said receiving steps comprise filtering said first and new hemodynamic signals to isolate low frequency data present therein.

15. The method of claim 14, wherein said filtering step comprises filtering said first and new hemodynamic signals with a low pass filter having a cutoff frequency of about one Hertz.

16. The method of claim 14, wherein said filtering step comprises filtering said first and new hemodynamic signals with a band pass filter having a pass band between about 0.1 and about 1.0 Hz.

17. The method of claim 14, wherein said filtering step comprises filtering said first and new hemodynamic signals with a band pass filter having a pass band between about 0.03 and about 1.0 Hz.

18. A method for optimizing pacing rate cutoff in an implantable cardiac device, comprising:
    (a) establishing a first pacing rate;
    (b) receiving a first hemodynamic signal representative of said first pacing rate;
    (c) establishing a second pacing rate;
    (d) receiving a second hemodynamic signal representative of said second pacing rate;
    (e) performing a comparison of said first and second hemodynamic signals;
    (f) repeating steps (c) through (e) until no further comparisons are desired; and
    (g) selecting a pacing rate based on said comparisons.

19. The method of claim 18, wherein said receiving steps comprise filtering said first and second hemodynamic signals to isolate low frequency data present therein.

20. The method of claim 19, wherein said filtering step comprises filtering said first and second hemodynamic signals with a low pass filter having a cutoff frequency of about one Hertz.

21. The method of claim 19, wherein said filtering step comprises filtering said first and second hemodynamic signals with a band pass filter having a pass band between about 0.1 and about 1.0 Hz.

22. The method of claim 9, wherein said filtering step comprises filtering said first and second hemodynamic signals with a band pass filter having a pass band between about 0.03 and about 1.0 Hz.

23. A method for optimizing a parameter in an implantable cardiac therapy device (ICTD), comprising:
   (a) receiving a hemodynamic signal generated by echocardiography;
   (b) filtering said hemodynamic signal to isolate low frequency data present therein;
   (c) sampling said low frequency data according to a sample algorithm metric; and
   (d) adjusting the parameter based on an analysis of said sampled low frequency data.

24. The method of claim 23, wherein said sampling step comprises sampling said low frequency data present in a portion of a frequency spectrum of said hemodynamic signal that is less than about one Hertz (1 Hz).

25. A method for optimizing a parameter in an implantable cardiac therapy device (ICTD), comprising:
   (a) receiving a hemodynamic signal representing blood pressure;
   (b) filtering said hemodynamic signal to isolate low frequency data present therein;
   (c) sampling said low frequency data according to a sample algorithm metric; and
   (d) adjusting the parameter based on an analysis of said sampled low frequency data.

26. The method of claim 25, wherein said sampling step comprises sampling said low frequency data present in a portion of a frequency spectrum of said hemodynamic signal that is less than about one Hertz (1 Hz).

27. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) adjusting an atrio-ventricular delay based on an analysis of said sampled low frequency data.

28. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) adjusting an inter-ventricular delay based on an analysis of said sampled low frequency data.

29. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) adjusting a voltage level for arrhythmia treatment based on an analysis of said sampled low frequency data.

30. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) selecting an arrhythmia treatment modality based on an analysis of said sampled low frequency data.

31. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) adjusting lead placement based on an analysis of said sampled low frequency data.

32. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) selecting pacing electrodes based on an analysis of said sampled low frequency data.

33. A method for optimizing a parameter in an implantable cardiac therapy device (ICTD), comprising:
   (a) receiving a hemodynamic signal;
   (b) filtering said hemodynamic signal to isolate low frequency data present therein;
   (c) sampling said low frequency data according to a sample algorithm metric; and
   (d) adjusting a pacing rate cutoff for the ICTD based on an analysis of said sampled low frequency data.

* * * * *